US006475494B2

(12) United States Patent
Kaiko et al.

(10) Patent No.: US 6,475,494 B2
(45) Date of Patent: *Nov. 5, 2002

(54) OPIOID AGONIST/ANTAGONIST COMBINATIONS

(75) Inventors: Robert F. Kaiko, Weston, CT (US); Robert D. Colucci, Newton, CT (US)

(73) Assignee: Euro-Celtique S.A., Luxembourg (LU)

(*) Notice: Subject to any disclaimer, the term of this patent is extended or adjusted under 35 U.S.C. 154(b) by 0 days.

This patent is subject to a terminal disclaimer.

(21) Appl. No.: 09/815,167

(22) Filed: Mar. 22, 2001

(65) Prior Publication Data

US 2002/0013301 A1 Jan. 31, 2002

Related U.S. Application Data

(63) Continuation of application No. 09/218,662, filed on Dec. 22, 1998, now Pat. No. 6,277,384.
(60) Provisional application No. 60/068,480, filed on Dec. 22, 1997.

(51) Int. Cl.[7] ............... A61K 9/00; A61K 9/48; A61K 9/20; A61K 31/44; A01N 43/42
(52) U.S. Cl. ............ 424/400; 424/451; 424/464; 514/282; 514/284; 514/810; 514/812
(58) Field of Search ............... 424/400, 451, 424/464; 514/282, 289, 810, 812

(56) References Cited

U.S. PATENT DOCUMENTS

| | | | |
|---|---|---|---|
| 2,770,569 A | 11/1956 | Fromherz et al. | 167/65 |
| 3,332,950 A | 7/1967 | Blumberg et al. | 260/285 |
| 3,493,657 A | 2/1970 | Lewenstein et al. | 424/260 |
| 3,676,557 A | 7/1972 | Lachman et al. | 424/260 |
| 3,773,955 A | 11/1973 | Pachter et al. | 424/260 |
| 3,879,555 A | 4/1975 | Pachter et al. | 424/260 |
| 3,966,940 A | 6/1976 | Pachter et al. | 424/260 |

(List continued on next page.)

FOREIGN PATENT DOCUMENTS

| | | | |
|---|---|---|---|
| DE | 2 222039 | 11/1972 | A61K/27/00 |
| DE | 4325465 | 2/1995 | A61K/31/485 |
| DE | 29 719704 | 2/1997 | A61K/31/485 |
| DE | 19 651551 | 6/1998 | A61K/31/485 |
| EP | 0205282 | 12/1986 | A61K/9/22 |
| EP | 0352361 | 1/1990 | A61K/31/485 |
| EP | 0913152 | 6/1999 | A61K/31/485 |
| WO | WO 83 03197 | 9/1983 | A61K/9/22 |
| WO | WO 94 06426 | 3/1994 | A61K/31/46 |
| WO | WO 95 03804 | 2/1995 | A61K/31/485 |
| WO | WO 96 02251 | 2/1996 | A61K/31/485 |
| WO | WO 97 33566 | 9/1997 | A61K/9/20 |
| WO | WO 98 35679 | 8/1998 | A61K/31/485 |

OTHER PUBLICATIONS

Gan et al., "Opioid–sparing Effects of a Low–dose Infusion of Naloxone in Patient–administered Morphine Sulfate.", Anesthesiology, vol. 87(5), (1997) pp. 1075–1080.
Sunshine, et. al., "Analgesic Efficacy of Pentazocine Versus a Pentazocine–Naloxone Combination Following Oral Administration", Clin. J. Pain 1988; 4:35–40.
Wang, et. al., "Crossover and Parallel Study of Oral Analgesics". J. Clin. Pharmacol 1981; 21:162–8.

(List continued on next page.)

Primary Examiner—Thurman K. Page
Assistant Examiner—Todd D Ware
(74) Attorney, Agent, or Firm—Davidson, Davidson & Kappel, LLC

(57) ABSTRACT

The invention is directed in part to oral dosage forms comprising a combination of an orally analgesically effective amount of an opioid agonist and an orally active opioid antagonist, the opioid antagonist being included in a ratio to the opioid agonist to provide a combination product which is analgesically effective when the combination is administered orally, but which is aversive in a physically dependent subject. Preferably, the amount of opioid antagonist included in the combination product provides at least a mildly negative, "aversive" experience in physically dependent addicts (e.g., precipitated abstinence syndrome).

23 Claims, 11 Drawing Sheets

U.S. PATENT DOCUMENTS

| | | | |
|---|---|---|---|
| 4,176,186 A | 11/1979 | Goldberg | 424/260 |
| 4,401,672 A | 8/1983 | Portoghese | 424/260 |
| 4,451,470 A | 5/1984 | Ganti | 424/260 |
| 4,457,933 A | 7/1984 | Gordon et al. | 424/260 |
| 4,464,378 A | 8/1984 | Hussain et al. | 424/260 |
| 4,573,995 A | 3/1986 | Chen et al. | 604/896 |
| 4,582,835 A | 4/1986 | Lewis et al. | 514/282 |
| 4,608,376 A | 8/1986 | Pasternak | 514/282 |
| 4,661,492 A | 4/1987 | Lewis et al. | 514/282 |
| 4,719,215 A | 1/1988 | Goldberg | 514/282 |
| 4,730,048 A | 3/1988 | Portoghese et al. | 546/45 |
| 4,760,069 A | 7/1988 | Rzeszotarski et al. | 514/282 |
| 4,769,372 A | 9/1988 | Kreek et al. | 514/282 |
| 4,785,000 A | 11/1988 | Kreek et al. | 514/282 |
| 4,803,208 A | 2/1989 | Pasernak | 514/282 |
| 4,806,341 A | 2/1989 | Chien et al. | 424/448 |
| 4,806,543 A | 2/1989 | Choi et al. | 514/464 |
| 4,806,558 A | 2/1989 | Wuest et al. | 514/381 |
| 4,861,598 A | 8/1989 | Oshlack | 424/468 |
| 4,861,781 A | 8/1989 | Goldberg | 514/282 |
| 4,873,076 A | 10/1989 | Fishman et al. | 424/10 |
| 4,882,335 A | 11/1989 | Sinclair | 514/282 |
| 4,889,860 A | 12/1989 | Rzeszotarski et al. | 514/282 |
| 4,935,428 A | 6/1990 | Lewis | 514/282 |
| 5,075,341 A | 12/1991 | Mendelson et al. | 514/282 |
| 5,086,058 A | 2/1992 | Sinclair et al. | 514/282 |
| 5,096,715 A | 3/1992 | Sinclair | 424/449 |
| 5,102,887 A | 4/1992 | Goldberg | 514/282 |
| 5,149,538 A | 9/1992 | Granger et al. | 424/449 |
| 5,225,440 A | 7/1993 | London et al. | 514/535 |
| 5,236,714 A | 8/1993 | Lee | 424/449 |
| 5,256,669 A | 10/1993 | Askanazi et al. | 514/282 |
| 5,273,760 A | 12/1993 | Oshlack et al. | 424/480 |
| 5,316,759 A | 5/1994 | Rose et al. | 424/10 |
| 5,317,022 A | 5/1994 | Borsodi et al. | 514/282 |
| 5,321,012 A | 6/1994 | Mayer et al. | 514/25 |
| 5,352,680 A | 10/1994 | Portoghese et al. | 514/279 |
| 5,352,683 A | 10/1994 | Mayer et al. | 514/289 |
| 5,356,900 A | 10/1994 | Bihari et al. | 514/282 |
| 5,376,662 A | 12/1994 | Ockert | 514/282 |
| 5,426,112 A | 6/1995 | Zagon et al. | 514/282 |
| 5,457,208 A | 10/1995 | Portoghese et al. | 546/45 |
| 5,472,943 A | 12/1995 | Crain et al. | 514/12 |
| 5,486,362 A | 1/1996 | Kitchell et al. | 424/426 |
| 5,502,058 A | 3/1996 | Mayer et al. | 514/289 |
| 5,512,578 A | 4/1996 | Crain et al. | 514/282 |
| 5,514,680 A | 5/1996 | Weber et al. | 514/249 |
| 5,534,492 A | 7/1996 | Aston et al. | 514/608 |
| 5,556,838 A | 9/1996 | Mayer et al. | 514/25 |
| 5,574,052 A | 11/1996 | Rose et al. | 514/343 |
| 5,578,725 A | 11/1996 | Portoghese et al. | 546/35 |
| 5,580,876 A | 12/1996 | Crain et al. | 514/282 |
| 5,585,348 A | 12/1996 | Crain et al. | 514/12 |
| 5,616,601 A | 4/1997 | Khanna et al. | 514/399 |
| 5,624,932 A | 4/1997 | Qin et al. | 514/282 |
| 5,633,259 A | 5/1997 | Qin et al. | 514/282 |
| 5,767,125 A | 6/1998 | Crain et al. | 514/282 |
| 5,858,017 A | 1/1999 | Demopulos et al. | 604/890.1 |
| 5,860,950 A | 1/1999 | Demopulos et al. | 604/49 |
| 5,866,164 A | 2/1999 | Kuczynski et al. | 424/472 |
| 5,880,132 A | 3/1999 | Hill | 514/282 |
| 5,942,241 A | 8/1999 | Chasin et al. | 424/426 |
| 5,968,547 A | 10/1999 | Reder et al. | 424/449 |
| 5,972,954 A | 10/1999 | Foss | 514/282 |
| 5,998,434 A | 12/1999 | Mitch et al. | 514/305 |
| 6,228,863 B1 | 5/2001 | Palermo et al. | 514/282 |
| 6,277,384 B1 * | 8/2001 | Kaiko et al. | 424/400 |

OTHER PUBLICATIONS

Gonzalez JP, et. al., Naltrexone: A review of its Pharmacodynamic and Pharmacokinetic Properties and Therapeutic Efficacy in the Management of Opioid Dependence. Drugs 1988; 35:192–213.

Weinhold, LL, et al., Buprenorphine Alone and in Combination with Naltrexone in Non–Dependent Humans, Drug and Alcohol Dependence 1992; 30:263–274.

Mendelson J., et al., Buprenorphine and Naloxone Interactions in Opiate–Dependent Volunteers, Clin. Phar. Ther. 1996; 60:105–114.

Physician's Desk Reference 48th ed., 1994; 2120–2121, Montvale, NJ.

Crain, et. al., "Ultra–low concentrations of naloxone selectively antagonize excitory effects of morphine on sensory neurons, thereby increasing its antinociceptive potency and attenuating tolerance/dependence during chronic cotreatment", Proc. Natl. Acad. Sci. USA, 1995; vol. 92, 10540–10544.

Shen, et. al., "Ultra–low doses of naltrexone or etorphine increase morphine's antinocicpetive potency and attenuate tolerance/dependence in mice", Brain Research, 757:176–190 (1997).

Holmes, et. al., Anesth. Analg. 77:1166–73 (1993).

Miaskowski, et. al., Brain Research 596:41–45 (1992).

Vaccarino, et. al., Pain 36:103–109 (1989).

Cappel, et. al., Pharmacology Biochemistry & Behavior, vol. 34, pp. 425–427 (1989).

Chih–Cheng Chien, Neuroscience Letters 190 (1995) 137–139.

Translation of previously submitted German patent application DE 43 25 465.

Walsh et al., Effects of naltrexone on response to intravenous cocaine, hydromorphone and their combination in humans (1996).

Yuan et al., Drug and Alcohol Dependence 52 (1998) 161–165.

Yuan et al., Clinical Trials and Therapeutics, 61 (Apr. 1997) 467–475.

Foss et al., J Clin Pharmacol 33 (1993) 747–751.

Abstract, Cancer Chemother Pharmacol 1998; 42(4):287–91.

* cited by examiner

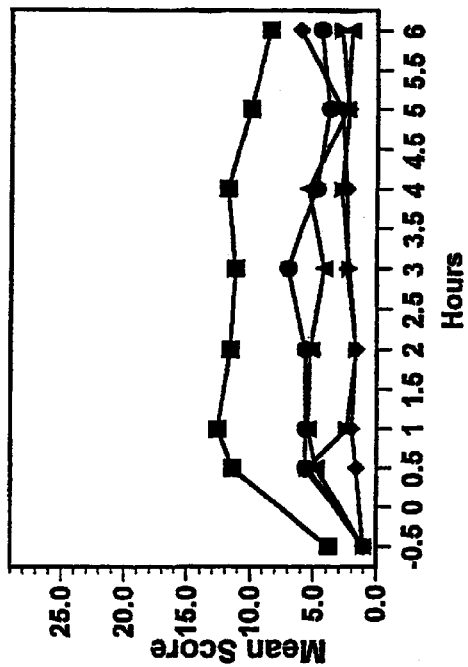
FIGURE 7A
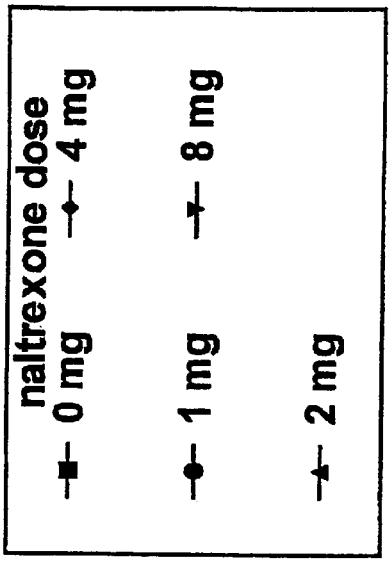
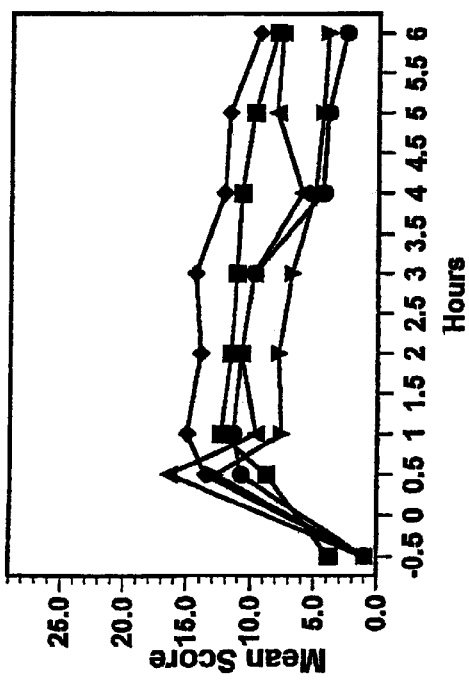
FIGURE 7B
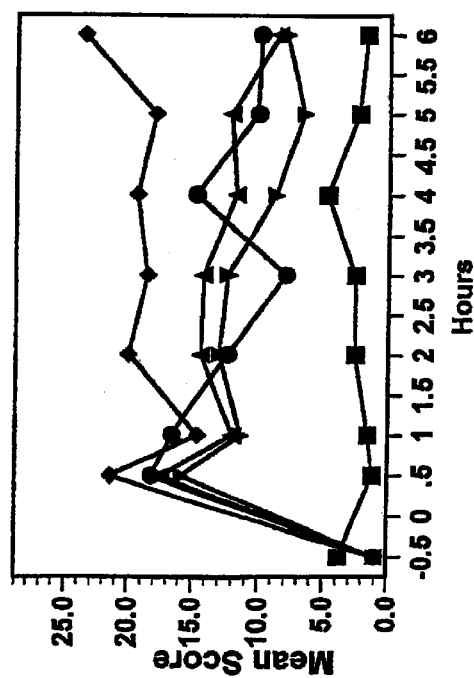
FIGURE 7C

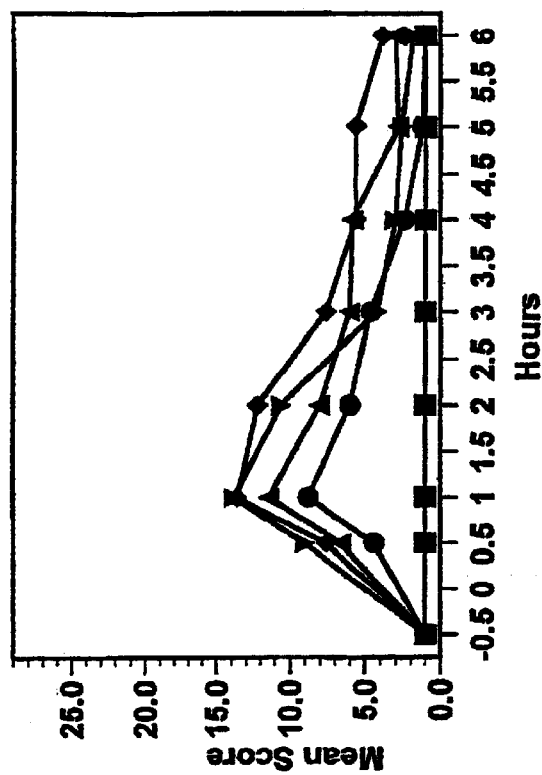
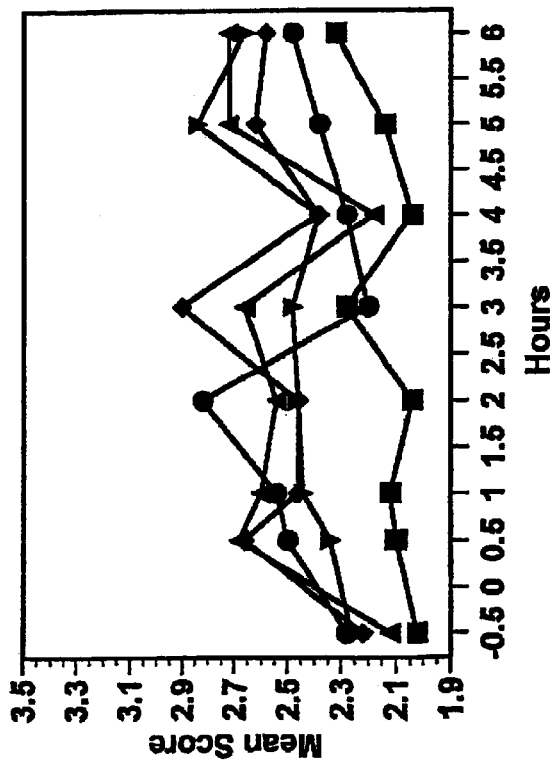
FIGURE 9A
FIGURE 9B
naltrexone dose
- 0 mg
- 1 mg
- 2 mg
- 4 mg
- 8 mg

OPIOID AGONIST/ANTAGONIST COMBINATIONS

This application is a continuation of U.S. patent application Ser. No. 09/218,662, filed on Dec. 22, 1998 now U.S. Pat. No. 6,277,384, issued on Aug. 21, 2001, which claims priority from U.S. Provisional Application Ser. No. 60/068,480, filed Dec. 22, 1997, hereby incorporated by reference.

BACKGROUND OF THE INVENTION

Opioids, also known as opioid agonists, are a group of drugs that exhibit opium or morphine-like properties. The opioids are employed primarily as moderate to strong analgesics, but have many other pharmacological effects as well, including drowsiness, respiratory depression, changes in mood and mental clouding without a resulting loss of consciousness. Opioids act as agonists, interacting with stereospecific and saturable binding sites in the brain and other tissues. Endogenous opioid-like peptides are present particularly in areas of the central nervous system that are presumed to be related to the perception of pain; to movement, mood and behavior, and to the regulation of neuroendocrinological functions. Opium contains more than twenty distinct alkaloids. Morphine, codeine and papaverine are included in this group.

By the middle of the nineteenth century, the use of pure alkaloids such as morphine rather than crude opium preparations began to spread throughout the medical world. Parenteral use of morphine tended to produce a more severe variety of compulsive drug use. The problem of addiction to opioids stimulated a search for potent analgesics that would be free of the potential to produce addiction. By 1967, researchers had concluded that the complex interactions among morphine-like drugs, antagonists, and what was then called "mixed agonist-antagonist" could best be explained by postulating the existence of more than one type of receptor for opioids and related drugs. With the advent of new totally synthetic entities with morphine-like actions, the term "opioid" was generally retained as a generic designation for all exogenous substances that bind stereospecifically to any of several subspecies of opioid receptors and produce agonist actions.

The potential for the development of tolerance and physical dependence with repeated opioid use is a characteristic feature of all the opioid drugs, and the possibility of developing psychological dependence (i.e., addiction) is one of the major concerns in the use of the treatment of pain with opioids, even though iatrogenic addiction is rare. Another major concern associated with the use of opioids is the diversion of these drugs from the patient in pain to another (non-patient) for recreational purposes, e.g., to an addict.

The overall abuse potential of an opioid is not established by any one single factor. Instead, there is a composite of factors, including, the capacity of the drug to produce the kind of physical dependence in which drug withdrawal causes sufficient distress to bring about drug-seeking behavior; the ability to suppress withdrawal symptoms caused by withdrawal from other agents; the degree to which it induces euphoria similar to that produced by morphine and other opioids; the patterns of toxicity that occur when the drug is dosed above its normal therapeutic range; and physical characteristics of the drugs such as water solubility. Such physical characteristics may determine whether the drug is likely to be abused by the parenteral route.

In the United States, the effort to control the compulsive drug user includes efforts to control drug availability by placing restrictions on the use of opioids in the treatment of pain of compulsive drug users. In practice, the physician is often faced with a choice of administering potent opioid analgesics even to persons who seem predisposed to develop psychological dependence, i.e., addiction, on such drugs. In view of this problem, it has been recommended that these patients should not be given an opioid when another drug without a potential for abuse will suffice; and further that these patients should not be permitted to self-administer such drugs parenterally and should only be given a few days' supply at a time.

At least three basic patterns of opioid use and dependence have been identified. The first involves individuals whose drug use begins in the context of medical treatment and who obtain their initial supplies through, e.g., physicians. Another pattern begins with experimental or "recreational" drug use and progresses to more intensive use. A third pattern involves users who begin in one or another of the preceding ways but later switch to oral opioids such as methadone, obtained from organized addiction treatment programs.

Tolerance refers to the need to increase the dose of opioid over a period of time in order to achieve the same level of analgesia or euphoria, or the observation that repeated administration of the same dose results in decreased analgesia, euphoria, or other opioid effects. It has been found that a remarkable degree of tolerance develops to the respiratory depressant, analgesic, sedative, emetic and euphorigenic effects of opioids. However, the rate at which this tolerance may develop in either an addict or in a patient requiring treatment of pain, depends on the pattern of use. If the opioid is used frequently, it may be necessary to increase the dose. Tolerance does not develop equally or at the same rate to all the effects of opioids, and even users who are highly tolerant to respiratory depressant effects continue to exhibit miosis and constipation. Tolerance to opioids largely disappears when the withdrawal syndrome has been completed.

Physical dependence may develop upon repeated administrations or extended use of opioids. Physical dependence is gradually manifested after stopping opioid use or is precipitously manifested (e.g., within 20 minutes) after administration of a narcotic antagonist (referred to "precipitated withdrawal"). Depending upon the drug to which dependence has been established and the duration of use and dose, symptoms of withdrawal vary in number and kind, duration and severity. The most common symptoms of the withdrawal syndrome include anorexia, weight loss, pupillary dilation, chills alternating with excessive sweating, abdominal cramps, nausea, vomiting, muscle spasms, hyperirritability, lachrymation, rinorrhea, goose flesh and increased heart rate. Abstinence syndrome typically begins to occur 24–48 hours after the last dose, and the syndrome reaches its maximum intensity about the third day and may not begin to decrease until the third week.

Psychological dependence (i.e., addiction) on opioids is characterized by drug-seeking behavior directed toward achieving euphoria and escape from, e.g., psychosocioeconornic pressures. An addict will continue to administer opioids for non-medicinal purposes and in the face of self-harm.

Pharmacologically, opioid antagonists typically block or reverse all of the effect of opioid agonists. One use of opioid antagonists is as a once-a-day treatment of naltrexone to block euphoric effects that might be otherwise obtained upon administration of opioids to addicts. Small doses of opioid antagonists have been used to determine whether individuals are physically dependent on opioids. Most commonly, opioid antagonists are used to reverse the effects of opoids on individuals who have overdosed on opioid agonist drugs.

There have previously been attempts in the art to control the abuse potential associated with opioid analgesics. Typically, a particular dose of an opioid analgesic is more potent when administered parenterally as compared to the same dose administered orally. Therefore, one popular mode of abuse of oral medications involves the extraction of the opioid from the dosage form, and the subsequent injection of the opioid (using any "suitable" vehicle for injection) in order to achieve a "high." Attempts to curtail abuse have therefore typically centered around the inclusion in the oral dosage form of an opioid antagonist which is not orally active but which will substantially block the analgesic effects of the opioid if one attempts to dissolve the opioid and administer it parenterally.

For example, the combination of pentazocine and naloxone has been utilized in tablets available in the United States, commercially available as Talwin®Nx from Sanofi-Winthrop. Talwin®Nx contains pentazocine hydrochloride equivalent to 50 mg base and naloxone hydrochloride equivalent to 0.5 mg base. Talwin®Nx is indicated for the relief of moderate to severe pain. The amount of naloxone present in this combination has no action when taken orally, and will not interfere with the pharmacologic action of pentazocine. However, this amount of naloxone given by injection has profound antagonistic action to narcotic analgesics. Thus, the inclusion of naloxone is intended to curb a form of misuse of oral pentazocine which occurs when the dosage form is solubilized and injected. Therefore, this dosage has lower potential for parenteral misuse than previous oral pentazocine formulations. However, it is still subject to patient misuse and abuse by the oral route, for example, by the patient taking multiple doses at once.

Sunshine, et al. "Analgesic Efficacy of Pentazocine Versus a Pentazocine-Naloxone Combination Following Oral Administration", Clin. J. Pain, 1988:4:35–40, reported on the effect of the addition of 0.5 mg naloxone on the analgesic efficacy of pentazocine 50 mg. The combination was found to be significantly less efficacious than pentazocine for the sum of the pain intensity difference (SPID), and for relief and pain intensity difference (PID) at the fourth hour. For patients with moderate baseline pain, the combination produced significantly less pain relief than pentazocine for SPID and for relief and PID at hours 3 and 4. In patients with severe baseline pain, there was no significant difference found between pentazocine and the combination of pentazocine plus naloxone.

Wang, et al. "Crossover and Parallel Study of Oral Analgesics", J. Clin Pharmacol 1981; 21:162–8, studied the combination of naloxone 0.25 mg and Percodan® (composed of 4.5 mg oxycodone HCl, oxycodone terephthalate 0.28 mg, aspirin 224 mg, phenacetin 160 mg, and caffeine 32 mg) compared to Percodan® alone, and placebo in a crossover study of patients with chronic pain. The combination had lower mean scores than Percodan® alone for most of the analgesic hourly parameters in the later hours of the trial. However, for the summary variables, the combination showed no significant difference from either placebo or Percodan®.

A fixed combination of buprenorphine and naloxone was introduced in 1991 in New Zealand (Temgesic®Nx, Reckitt & Colman) for the treatment of pain.

A fixed combination therapy comprising tilidine (50 mg) and naloxone (4 mg) has been available in Germany for the management of severe pain since 1978 (Valoron®N, Goedecke). The rationale for the combination of these drugs is effective pain relief and the prevention of tilidine addiction through naloxone-induced antagonisms at the morphine receptor.

U.S. Pat. No. 3,773,955 (Pachter, et al.) described orally effective analgetic compositions which upon parenteral administration do not produce analgesia, euphoria, or physical dependence, and thereby prevent parenteral abuse of the analgetic agents. Such compositions contained from about 0.1 mg to about 10 mg naloxone per analgetic oral dose. This reference was not concerned with oral abuse of opioids.

U.S. Pat. No. 3,493,657 (Lewenstein, et al.) described compositions comprising naloxone and morphine or oxymorphone, which compositions were said to provide a strong analgesic effect without the occurrence of undesired side effects such as hallucinations.

U.S. Pat. No. 4,457,933 (Gordon, et al.) described a method for decreasing both the oral and parenteral abuse potential of strong analgetic agents such as oxycodone, propoxyphene and pentazocine, by combining an analgesic dose of the opioid with naloxone in a specific, relatively narrow range. Oxycodone-naloxone compositions having a ratio of 2.5–5:1 parts by weight and pentazocine-naloxone compositions having a ratio of 16–50:1 parts by weight were preferred. The dose of naloxone which was to be combined with the opioid is stated to substantially eliminate the possibility of either oral or parenteral abuse of the opioid without substantially affecting the oral analgesic activity thereof.

U.S. Pat. No. 4,582,835 (Lewis) describes a method of treating pain by administering a sublingually effective dose of buprenorphine with naloxone. Lewis describes dosage ratios of naloxone to buprenorphine from 1:3 to 1:1 for parenteral administration, and from 1:2 to 2:1 for sublingual administration.

It has been increasingly recognized in the art that oral opioid formulations are not only being abused by the parenteral route, but also via the oral route when the patient or addict orally self-administers more than the prescribed oral dose during any dosage interval. There is therefore a need for the development of a formulation for the treatment of pain which is administrable orally and which provides a lower potential for oral abuse.

To the inventors'knowledge, a ratio of opigid agonist to opioid antagonist which would be analgesically effective when the combination is administered orally, but which is aversive in a physically dependent subject has not been recognized to date.

OBJECTS AND SUMMARY OF THE INVENTION

It is an object of the invention to provide an oral dosage form of an opioid analgesic which is subject to less abuse potential via the oral route than prior commercially available dosage forms.

It is a further object of the present invention to provide an oral dosage form of an opioid analgesic and method which provides therapeutic analgesia and which also provides a negative, "aversive" experience when a large amount of the opioid, e.g., about 2–3 times the usually prescribed dose, is taken by or administered to a physically dependent subject.

It is a further object of the present invention to provide an oral dosage form of an opioid analgesic and a method for providing therapeutic analgesia in a manner which is not as positively reinforcing in non-physically dependent subjects taking more than the usually prescribed dose, e.g., about 2–3 times the usually prescribed dose of the opioid, as compared to the same amount of opioid without the antagonist.

It is a further object of the invention to provide a method of treating pain in human patients with an oral dosage form of an opioid analgesic while reducing the oral abuse potential of dosage form.

It is a further object of the invention to provide a method of manufacturing an oral dosage form of an opioid analgesic such that it has less oral abuse potential.

The above objects and others are achieved by the present invention, which is directed in part to the surprising finding that there exists a ratio of opioid antagonist to opioid agonist (analgesic) which is analgesically effective when the combination is administered orally, but which is aversive in a physically dependent subject. To the inventor's knowledge, this was not even considered by those skilled in the art, e.g., an addictionologist, analgesiologist, a clinical pharmacologist. It is surprising that one combination product (of combined antagonist/agonist) could in essence be therapeutic to one population (patients in pain), while being unacceptable (aversive) in a different population (e.g., physically, dependent subjects) when administered at the same dose or at a higher dose than the usually prescribed dosage, e.g., about 2–3 times the usually prescribed dose of the opioid.

The present invention is directed in part to an oral dosage form comprising an orally analgesically effective amount of an opioid agonist and an opioid antagonist in a ratio which maintains analgesic efficacy by the opioid analgesic but which may decrease analgesia somewhat as assessed by direct measurement in patients or by the use of one or more surrogate measures of opioid efficacy (analgesia) in human subjects. Surrogate measures of opioid efficacy (analgesia) include sedation, respiratory rate and/or pupil size (via pupillometry), and visual analogue scale ("VAS") for "drug effect". Such surrogate measures are affected in a direction which indicates reduced opioid effect, as compared to the same dose of opioid without the concomitant dose of opioid antagonist.

In certain preferred embodiments where the opioid is hydrocodone and the antagonist is naltrexone, the oral dosage form includes hydrocodone in the form of its bitartrate salt and naltrexone in the form of its hydrochloride salt.

In certain preferred embodiments where the opioid is hydrocodone and the antagonist is naltrexone, the ratio of naltrexone to hydrocodone is preferably from about 0.03–0.27:1 by weight, and more preferably from about 0.05–0.20:1 by weight.

The present invention is directed to a method of preventing oral abuse of an oral opioid formulation by a subject, comprising preparing an oral dosage form which comprises an orally analgesically effective amount of an opioid agonist and an opioid antagonist in a ratio which maintains analgesic efficacy by the opioid analgesic but which may decrease analgesia somewhat as assessed by direct measurement in patients or by the use of one or more surrogate measures of opioid effect in human subjects. When the oral dosage form is taken by a physically dependent subject at a relatively large dosage, e.g., about 2–3 times the usually prescribed dose, that use is aversive in a physically dependent human subject and preferably not as positively reinforcing as the opioid (ingested alone) in a non-physically dependent human subject.

The present invention is also directed to a method of treatment, comprising orally administering an orally analgesically effective amount of an opioid agonist together with an opioid antagonist in a ratio which maintains analgesic efficacy by the opioid analgesic but which may decrease analgesia somewhat by direct measurement in patients or by the use of one or more surrogate measures of opioid effect in human subjects.

The present invention is further directed in part to oral dosage forms comprising a combination of an orally analgesically effective amount of an opioid agonist and an orally active opioid antagonist, the opioid antagonist being included in an amount (i) which does not cause a reduction in the level of analgesia elicited from the dosage form upon oral administration to a non-therapeutic level and (ii) which provides at least a mildly negative, "aversive" experience in physically dependent subjects (e.g., precipitated abstinence syndrome) when the subjects attempt to take at least twice the usually prescribed dose at a time (and often 2–3 times that dose or more), as compared to a comparable dose of the opioid without the opioid antagonist present. Preferably, the amount of naltrexone included in the oral dosage form is less positively reinforcing (e.g., less "liked") to a non-physically dependent opioid addict than a comparable oral dosage form without the antagonist included. Preferably, the formulation provides effective analgesia when orally administered.

For purposes of the present invention, the phrase "which may decrease analgesia somewhat as assessed by direct measurement in patients or by the use of one or more surrogate measures of opioid analgesic efficacy in human subjects" means that the patient in pain may or may not appreciably notice the difference between the formulation administered in accordance with the invention (i.e., combination of opioid agonist/antagonist) and a similar formulation which includes the same dose of opioid agonist without the opioid antagonist, but will obtain an analgesic effect from the combination. The pharmacodynamic effect (analgesia) of the formulations administered in accordance with the invention can be described by means of, for example, scores from an analgesic questionnaire reported by the patients at serial times following administration of the dosage form. Summary measures of analgesia include the sum of pain intensity difference (SPID) and total pain relief (TOTPAR).

In certain preferred embodiments, the amount of opioid antagonist included in the dosage form may cause a clinically significant reduction in the level of analgesia elicited from the dosage form upon oral administration, e.g., as measured by surrogate measures such as a Visual Analogue Scale ("VAS") for "drug effect". In other embodiments, the amount of opioid antagonist included in the oral dosage form may cause a noticeable reduction in the level of analgesia elicted from the dosage form upon oral administration, but does not reduce the level of analgesia provided to a subtherapeutic level.

Preferably, the amount of antagonist included in the oral dosage form is less positively reinforcing (e.g., less "liked") by a non-physically dependent opioid subject than a comparable oral dosage form without the antagonist included.

The present invention is also directed to a method of preparing an oral dosage form of an opioid analgesic intended for the treatment of pain in human patients in a manner which minimizes the likelihood of oral abuse of the dosage form, combining an orally analgesically effective amount of an opioid agonist together with an opioid antagonist in a ratio which maintains analgesic efficacy by the opioid analgesic but which may decrease analgesia somewhat by direct measurement in patients or by the use of one or more surrogate measures of analgesia in human subjects. In certain embodiments, the combination when orally administered-provides a clinically significant reduction in the level of analgesia elicited from the dosage form upon oral administration (as compared to the same dose of opioid alone), and provides at least a mildly negative, "aversive" experience in a physically dependent subject (e.g., precipitated abstinence syndrome) when the subject takes more than the usually prescribed or usual dose of opioid. The subject may be, for example, an addict who attempts to achieve euphoria (a "high") by taking more than (e.g., at least 2–3 times) the usually prescribed dose at a time. The amount of opioid antagonist included in the dosage form may or may not cause a noticeable reduction in the level of analgesia elicited from the dosage form upon oral administration, e.g., as measured by pharmacodynamic parameters such as a Visual Analogue Scale ("VAS") for drug effect, but preferably allows the dosage form to nevertheless provide effective analgesia. In certain preferred embodiments of the method, the dose of opioid antagonist appreciably affects a surrogate measure of opioid analgesic effect. In certain preferred embodiments, the amount of antagonist included in the oral dosage form is less positively reinforcing (e.g., less "liked") by a non-physically dependent subject than a comparable oral dosage form without the antagonist included.

The oral pharmaceutical compositions containing the inventive combination of drugs set forth herein may be in the form of tablets, liquids, troches, lozenges, aqueous or oily suspensions, multiparticulate formulations including dispersable powders, granules, matrix spheroids or coated inert beads, emulsions, hard or soft capsules or syrups or elixirs, microparticles (e.g., microcapsules, microspheres and the like), buccal tablets, etc. The dosage forms of the present invention may include any desired pharmaceutically acceptable excipients known to those skilled in the art. The dosage forms may further provide an immediate release of the opioid agonist and the opioid antagonist. In certain preferred embodiments, the dosage forms provide a sustained release of the opioid agonist, and provide the part or all of the dose of opioid antagonist in (i) immediate release form, (ii) sustained release form, or (iii) both immediate and sustained release form. Such embodiments may further comprise a portion of the opioid agonist in immediate release form. Sustained release may be accomplished in accordance with formulations/methods of manufacture known to those skilled in the art of pharmaceutical formulation, e.g., via the incorporation of a sustained release carrier into a matrix containing the opioid agonist and opioid antagonist; or via a sustained release coating of a matrix containing the opioid agonist and opioid antagonist.

The invention may provide for a safer product (eg, less respiratory depression) as well as one with a slower rate of opioid tolerance and physical dependency development.

In certain other preferred embodiments, the opioid included in the dosage form is a different orally active opioid agonist than hydrocodone. The ratio of naltrexone included in such formulations can be readily determined based on a simple calculation, taking into account the known equianalgesic dosages of various opioid analgesics as compared to hydrocodone. Equianalgesic dosages of various opioid analgesics are provided below, and are otherwise known to those skilled in the art, e.g, from Foley, K. "The Treatment of Cancer Pain;" N. Engl. J. Med. 1985;313:84–95, hereby incorporated by reference. In yet further aspects of this embodiment, a different opioid antagonist is substituted for naltrexone, using equiantagonistic doses thereof.

In certain embodiments, a combination of two opioid analgesics is included in the formulation. In further embodiments, one or more opioid analgesics is included and a further non-opioid drug is also included, in addition to the opioid antagonist. Such non-opioid drugs would preferably provide additional analgesia, and, include, for example, aspirin, acetaminophen, non-steroidal antiinflammatory drugs ("NSAIDS"), NMDA antagonists, and cycooxygenase-II inhibitors ("COX-II inhibitors"). In yet further embodiments, a non-opioid drug can be included which provides a desired effect other than analgesia, e.g., antitussive, expectorant, decongestant, or antihistamine drugs, and the like.

The term "parenterally" as used herein includes subcutaneous injections, intravenous, intramuscular, intrasternal injection or infusion techniques.

The term "effective analgesia" is defined for purposes of the present invention as a satisfactory reduction in or elimination of pain, along with a tolerable level of side effects, as determined by the human patient.

The term "sustained release" is defined for purposes of the present invention as the release of the drug (opioid analgesic) from the oral formulation at such a rate that blood (e.g., plasma) concentrations (levels) are maintained within the therapeutic range (above the minimum effective analgesic concentration or "WEAC") but below toxic levels over a period of time indicative of a twice-a-day or a once-a-day formulation.

The term "steady state" refers to a time when the rate of elimination of a drug is the same as the rate of absorption of that drug into the body.

For purposes of the present invention, the term "opioid agonist" is interchangeable with the term "opioid" or "opioid analgesic" and shall include the base of the opioid, mixed agonist-antagonists, partial agonists, pharmaceutically acceptable salts thereof, stereoisomers thereof, ethers and esters thereof, and mixtures thereof.

For purposes of the present invention, the term "opioid antagonist" shall include the base, pharmaceutically acceptable salts thereof, stereoisomers thereof, ethers and esters thereof, and mixtures thereof.

BRIEF DESCRIPTION OF THE DRAWINGS

The following drawings are illustrative of embodiments of the invention and are not meant to limit the scope of the invention as encompassed by the claims.

FIG. 7A illustrates the subjects' ability to feel the effect of hydrocodone in the presence of varying amounts of naltrexone in Example 3;

FIGS. 7B and 7C illustrate the subjects' favorable or unfavorable subjective experiences of hydrocodone in the presence of varying amounts of naltrexone, respectively, for Example 3;

FIG. 9A illustrates the effect on pupil size of hydrocodone in the presence of varying amounts of naltrexone in Example 3;

FIG. 9B illustrates the apparent extent of withdrawal from the effect of hydrocodone in the presence of varying amounts of naltrexone in Example 3, from the perspective of the observer;

DETAILED DESCRIPTION OF THE INVENTION

Figure 1:
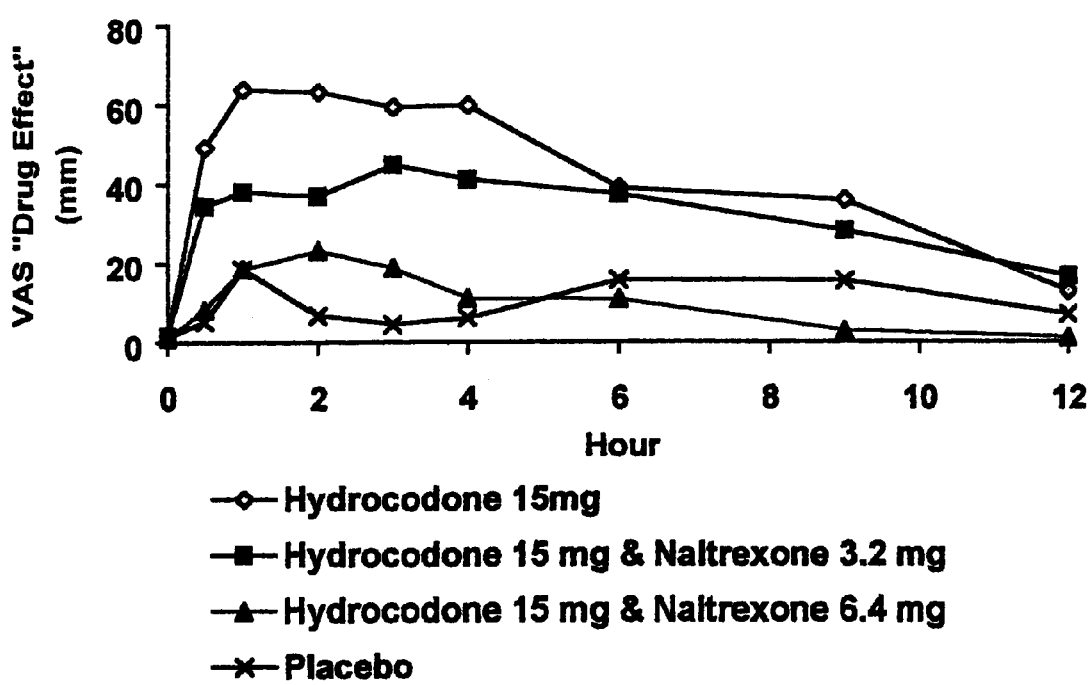
FIG. 1 shows the naltrexone antagonism of hydrocodone-induced VAS (Visual Analog Scale) "drug effect" for Example 1.

It has been postulated that there exists at least three subspecies of opioid receptors, designated mu, kappa, and delta. Within this framework, the mu receptor is considered to be involved in the production of superspinal analgesia, respiratory depression, euphoria, and physical dependence. The kappa receptor is considered to be involved in inducing spinal analgesia, miosis and sedation. Activation of the gamma receptors causes dysphoria and hallucinations, as well as respiratory and vasomotor stimulatory effects. A receptor distinct from the mu receptor and designated gamma has been described in the mouse vas deferens, Lord, et al. *Nature*, 1977, 267, 495–99. Opioid agonists are thought to exert their agonist actions primarily at the mu receptor and to a lesser degree at the kappa receptor. There are a few drugs that appear to act as partial agonists at one receptor type or another. Such drugs exhibit a ceiling effect. Such drugs include nalorphine, propiram, and buprenorphine. Still other drugs act as competitive antagonists at the mu receptor and block the effects of morphine-like drugs, by exerting agonist actions at the kappa and omega receptors. The term "agonist-antagonist" has evolved to describe such mechanism of actions. The concept of antagonism to the actions of opioids is considered to be complex.

It has been found with the administration of opioid agonist-antagonists and partial agonists that tolerance develops to the agonist effects but not to the antagonist effects of the drugs. Even after prolonged administration of high doses, discontinuance of naloxone is not characterized by any recognizable withdrawal syndrome, and withdrawal of naltrexone, another relatively pure opioid antagonist, produces very few signs and symptoms. However, after prolonged administration of high dosage, abrupt discontinuation of opioid agonist-antagonists nalorphine or cyclazocine causes a characteristic withdrawal syndrome that is similar for both drugs.

Naloxone is an opioid antagonist which is almost void of agonist effects. Subcutaneous doses of up to 12 mg of naloxone produce no discernable subjective effects, and 24 mg naloxone causes only slight drowsiness. Small doses (0.4–0.8 mg) of naloxone given intramuscularly or intravenously in man prevent or promptly reverse the effects of morphine-like opioid agonist. One mg of naloxone intravenously has been reported to completely block the effect of 25 mg of heroin. The effects of naloxone are seen almost immediately after intravenous administration. The drug is absorbed after oral administration, but has been reported to be metabolized into an inactive form rapidly in its first passage through the liver such that it has been reported to be only one fiftieth as potent as when parenterally administered. Oral dosage of more than 1 g have been reported to be almost completely metabolized in less than 24 hours.

Other opioid antagonists, for example, cyclazocine and naltrexone, both of which have cyclopropylmethyl substitutions on the nitrogen, retain much of their efficacy by the oral route and their durations of action are much longer, approaching 24 hours after oral doses. A most preferred opioid antagonist is naltrexone. However, equiantagonistic oral doses of other opioid antagonists, including but not limited to naloxone, nalmephene, cyclazocine, and levallorphan can be utilized in accordance with the present invention. The ratio of such other antagonists to a particular opioid agonist can be readily determined without undue experimentation by one skilled in art who desires to utilize a different opioid antagonist than naltrexone, the ratio of which to opioid agonists is exemplified and discussed in detail herein. Those skilled in the art may determine such ratios of other antagonists to opioid agonists, e.g., by conducting the same or similar clinical studies set forth in the examples appended herein. Thus, combinations of opioid antagonists/opioid agonists which are orally administered in ratios which are equivalent to the ratio of, e.g., naltrexone to hydrocodone set forth herein are considered to be within the scope of the present invention and within the scope of the appended claims. For example, in certain embodiments of the invention, naloxone is utilized as the opioid antagonist, the amount of naloxone included in the dosage form being large enough to provide an equiantagonistic effect as if naltrexone were included in the combination.

In the treatment of patients previously addicted to opioids, naltrexone has been used in large oral doses (over 100 mg) to prevent euphorigenic effects of opioid agonists. Naltrexone has been reported to exert strong preferential blocking action against mu over delta sites. Naltrexone is known as a synthetic congener of oxymorphone with no opioid agonist properties, and differs in structure from oxymorphone by the replacement of the methyl group located on the nitrogen atom of oxymorphone with a cyclopropylmethyl group. The hydrochloride salt of naltrexone is soluble in water up to about 100mg/cc. The pharmacological and pharmacokinetic properties of naltrexone have been evaluated in multiple animal and clinical studies. See, e.g., Gonzalez J P, et al. Naltrexone: A review of its Pharmacodynamic and Pharmacokinetic Properties and Therapeutic Efficacy in the Management of Opioid Dependence. *Drugs* 1988; 35:192–213, hereby incorporated by reference. Following oral administration, naltrexone is rapidly absorbed (within 1 hour) and has an oral bioavailability ranging from 5–40%. Naltrexone's protein binding is approximately 21% and the volume of distribution following single-dose administration is 16.1 L/kg.

Naltrexone is commercially available in tablet form (Revia®, DuPont) for the treatment of alcohol dependence and for the blockade of exogenously administered opioids. See, e.g., Revia (naltrexone hydrochloride tablets). *Physician's Desk Reference* 51$^{st}$ ed., Montvale, N.J. "Medical Economics" 1997;51:957–959. A dosage of 50mg ReVia® blocks the pharmacological effects of 25mg IV administered heroin for up to 24 hours.

It is known that when coadministered with morphine, heroin or other opioids on a chronic basis, naltrexone blocks the development of physical dependence to opioids. It is believed that the method by which naltrexone blocks the effects of heroin is by competitively binding at the opioid receptors. Naltrexone has been used to treat narcotic addiction by complete blockade of the effects of opioids. It has been found that the most successful use of naltrexone for a narcotic addiction is with good prognosis narcotic addicts as part of a comprehensive occupational or rehabilitative program involving behavioral control or other compliance enhancing methods. For treatment of narcotic dependence with naltrexone, it is desirable that the patient be opioid-free for at least 7–10 days. The initial dosage of naltrexone for such purposes has typically been about 25 mg, and if no withdrawal signs occur, the dosage may be increased to 50 mg per day. A daily dosage of 50 mg is considered to produce adequate clinical blockade of the actions of parenterally administered opioids. Naltrexone has also been used for the treatment of alcoholism as an adjunct with social and psychotherapeutic methods.

In the dosage forms and methods of the invention, the amount of naltrexone included is significantly less than the dosages previously commercially available. This is in part because the use of naltrexone is different in the present invention: the goal is not to block opioid effects, but rather to provide a negative, "aversive" experience when a large amount of the combination product, e.g., about 2–3 times the usually prescribed dose, is taken by or administered to a physically dependent subject.

Thus, for example, in formulations of the present invention in which the opioid is hydrocodone bitartrate 15 mg, the amount of naltrexone hydrochloride included in the formulation is from about 0.5 mg to about 4 mg, and preferably from about 0.75 mg to about 3 mg naltrexone per 15 mg hydrocodone.

Opioid analgesics which are useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propoxyphene, sufentanil, tilidine, tramadol, mixtures of any of the foregoing, salts of any of the foregoing, and the like.

In certain preferred embodiments, the opioid agonist or analgesic is selected from the group consisting of hydrocodone, morphine, hydromorphone, oxycodone, codeine, levorphanol, meperidine, methadone, or salts thereof, or mixtures thereof. In certain preferred embodiments, the opioid agonist is hydrocodone. Equianalgesic doses of these opioids, in comparision to a 15 mg dose of hydrocodone, are set forth in Table 1 below:

TABLE 1

Equianalgesic Doses of Opiolds

| Oploid | Calculated Dose (mg) |
| --- | --- |
| Oxycodone | 13.5 |
| Codeine | 90.0 |
| Hydrocodone | 15.0 |
| Hydromorphone | 3.375 |
| Levorphanol | 1.8 |
| Meperidine | 135.0 |
| Methadone | 9.0 |
| Morphine | 27.0 |

Based on the preferred ratio of naltrexone in an amount from about 0.5 to about 4 mg per 15 mg of hydrocodone, the approximate ratio of naltrexone to 1 mg of each opioid is set forth in Table 2:

TABLE 2

Weight Ratio of Naltrexone per Dose Opioid

| Opioid | Weight Ratio Naltrexone per 1 mg Opioid |
| --- | --- |
| Oxycodone | 0.037 to 0.296 |
| Codeine | 0.005 to 0.044 |
| Hydrocodone | 0.033 to 0.267 |
| Hydromorphone | 0.148 to 1.185 |
| Levorphanol | 0.278 to 2.222 |
| Meperidine | 0.0037 to 0.0296 |
| Methadone | 0.056 to 0.444 |
| Morphine | 0.018 to 0.148 |

Based on the more preferred ratio of about 0.75 mg to about 3 mg naltrexone per 15 mg hydrocodone of naltrexone, the approximate ratio of naltrexone to 1 mg of each opioid is set forth in Table 3:

TABLE 3

Weight Ratio of Naltrexone per Dose Opioid

| Opioid | Weight Ratio Naltrexone |
| --- | --- |
| Oxycodone | 0.056 to 0.222 |
| Codeine | 0.0083 to 0.033 |
| Hydrocodone | 0.050 to 0.200 |
| Hydromorphone | 0.222 to 0.889 |
| Levorphanol | 0.417 to 1.667 |
| Meperidine | 0.0056 to 0.022 |
| Methadone | 0.083 to 0.333 |
| Morphine | 0.028 to 0.111 |

Although hydrocodone is effective in the management of pain, there has been an increase in its abuse by individuals who are psychologically dependent on opioids or who misuse opioids for non-therapeutic reasons. Previous experience with other opioids has demonstrated a decreased abuse potential when opioids are administered in combination with a narcotic antagonist especially in patients who are ex-addicts. Weinhold L L, et al. Buprenorphine Alone and in Combination with Naltrexone in Non-Dependent Humans, *Drug and Alcohol Dependence* 1992; 30:263–274; Mendelson J., et. al., Buprenorphine and Naloxone Interactions in Opiate-Dependent Volunteers, *Clin Pharm Ther* 1996; 60:105–114; both of which are hereby incorporated by reference.

Hydrocodone is a semisynthetic narcotic analgesic and antitussive with multiple central nervous system and gastrointestinal actions. Chemically, hydrocodone is 4,5-epoxy-3-methoxy-17-methylmorphinan-6-one, and is also known as dihydrocodeinone. Like other opioids, hydrocodone may be habit forming and may produce drug dependence of the morphine type. In excess doses hydrocodone, like other opium derivatives, will depress respiration.

Oral hydrocodone is also available in Europe (Belgium, Germany, Greece, Italy, Luxembourg, Norway and Switzerland) as an antitussive agent. A parenteral formulation is also available in Germany as an antitussive agent. For use as an analgesic, hydrocodone bitartrate is commercially available in the United States only as a fixed combination with non-opiate drugs (i.e., ibuprofen, acetaminophen, aspirin, etc.) for relief of moderate or moderately severe pain.

A common dosage form of hydrocodone is in combination with acetaminophen, and is commercially available, e.g., as Lortab® in the U.S. from UCB Pharma, Inc. as 2.5/500 mg, 5/500 mg, 7.5/500 mg and 10/500 mg hydrocodone/acetaminophen tablets. Tablets are also available in the ratio of 7.5 mg hydrocodone bitartrate and 650 mg acetaminophen; and 7.5 mg hydrocodone bitartrate and 750 mg acetaminophen. Hydrocodone in combination with aspirin is given in an oral dosage form to adults generally in 1-2 tablets every 4-6 hours as needed to alleviate pain. The tablet form is 5mg hydrocodone bitartrate and 224 mg aspirin with 32 mg caffeine; or 5 mg hydrocodone bitartrate and 500 mg aspirin. A relatively new formulation comprises hydrocodone bitartrate and ibuprofen. Vicoprofen®, commercially available in the U.S. from Knoll Laboratories, is a tablet containing 7.5 mg hydrocodone bitartrate and 200 mg ibuprofen. The present invention is contemplated to encompass all such formulations, with the inclusion of the orally active opioid antagonist within the inventive amounts set forth herein.

The abuse potential of opioid analgesics such as hydrocodone is surprisingly curtailed by the inventive combinations of the present invention. More particularly, it has been discovered that it is possible to combine in a single oral dosage form an opioid analgesic together with a small amount of opioid antagonist, to achieve a product which still provides analgesia but which substantially negates the possibility that a physically dependent human subject will continue to abuse the drug by taking more than one tablet at a time, e.g., 2-3 times more than the usually prescribed dose.

The oral dosage forms of the invention comprise an orally therapeutically effective amount of an opioid agonist, together with an opioid antagonist such as naltrexone in an amount (i) which does not cause a reduction in the level of analgesia elicited from the dosage form upon oral administration to a non-therapeutic level and (ii) which provides at least a mildly negative, "aversive" experience in physically dependent human subjects, for example, physically dependent addicts (e.g., precipitated abstinence syndrome) when taking more than the usually prescribed dose at a time. Preferably, the amount of antagonist included in the oral dosage form is (iii) less positively reinforcing (e.g., less "liked" ) by a non-physically dependent human subject, e.g., opioid addict, than a comparable oral dosage form without the antagonist included.

The amount of antagonist which is useful to achieve parameters (i)–(iii) set forth in the preceding paragraph may be determined at least in part, for example, through the use of "surrogate" tests, such as a VAS scale (where the subject grades his/her perception of the effect of the dosage form) and/or via a measurement such as pupil size (measured by pupillometry). Such measurements allow one skilled in the art to determine the dose of antagonist relative to the dose of agonist which causes a diminution in the opiate effects of the agonist. Subsequently, one skilled in the art can determine the level of opioid antagonist that causes aversive effects in physically dependent subjects as well as the level of opioid antagonist that minimizes "liking scores" or opioid reinforcing properties in non-physically dependent addicts. Once these levels of opioid antagonist are determined, it is then possible to determine the range of antagonist dosages at or below this level which would be useful in achieving parameters (i)–(iii) set forth in the preceding paragraph.

The combination of opioid agonist and opioid antagonist can be employed in admixtures with conventional excipients, i.e., pharmaceutically acceptable organic or inorganic carrier substances suitable for oral administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For oral administration, particularly suitable are tablets, dragees, liquids, drops, suppositories, or capsules, caplets and gelcaps. The compositons intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combination of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed.

The method of treatment and pharmaceutical formulations of the present invention may further include one or more drugs in addition to the opioid analgesic and opioid antagonist, which additional drug(s) may or may not act synergistically therewith. Thus, in certain embodiments, a combination of two opioid analgesics may be included in the formulation, in addition to the opioid antagonist. For example, the, dosage form may include two opioid analgesics having different properties, such as half-life, solubility, potency, and a combination of any of the foregoing. In yet further embodiments, one or more opioid analgesics is included and a further non-opioid drug is also included, in addition to the opioid antagonist. Such non-opioid drugs would preferably provide additional analgesia, and include, for example, aspirin; acetaminophen; non-sterioidal antiinflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cycooxygenase-II inhibitors ("COX-II inhibitors"); and/or glycine receptor antagonists.

In certain preferred embodiments of the present invention, the invention allows for the use of lower doses of the opioid analgesic by virtue of the inclusion of an additional non-opioid agonist, such as an NSAID or a COX-2 inhibitor. By using lower amounts of either or both drugs, the side effects associated with effective pain management in humans are reduced.

Suitable non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zido-metacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, d-methadone or pharmaceutically acceptable salts thereof. For purposes of the present invention, the term "NMDA antagonist" is also deemed to encompass drugs that block a major intracellular consequence of NMDA-receptor activation, e.g. a ganglioside such as $GM_1$ or $GT_{1b}$ a phenothiazine such as trifluoperazine or a naphthalenesulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et.al.), and to treat chronic pain in U.S. Pat. No. 5,502,058 (Mayer, et. al.), all of which are hereby incorporated by reference. The NMDA antagonist may be included alone, or in combination with a local anesthetic such as lidocaine, as described in these Mayer, et.al. patents.

The treatment of chronic pain via the use of glycine receptor antagonists and the identification of such drugs is described in U.S. Pat. No. 5,514,680 (Weber, et al.), hereby incorporated by reference.

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain preferred COX-2 inhibitors include celecoxib (SC-58635), DUP-697, flosulide (CGP-28238), meloxicam, 6-methoxy-2 naphthylacetic acid (6-MNA), MK-966, nabumetone (prodrug for 6-MNA), nimesulide, NS-398, SC-5766, SC-58215, T-614; or combinations thereof Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic.

In yet further embodiments, a non-opioid drug can be included which provides a desired effect other than analgesia, e.g., antitussive, expectorant, decongestant, antihistamine drugs, local anesthetics, and the like.

An oral dosage form according to the invention may be provided as, for example, granules, spheroids, beads, pellets (hereinafter collectively referred to as "multiparticulates"). An amount of the multiparticulates which is effective to provide the desired dose of opioid over time may be placed in a capsule or may be incorporated in any other suitable oral solid form. Alternatively, the oral dosage form may be in the form of a tablet.

Controlled Release Dosage Forms

The opioid agonist/opioid antagonist combination can be formulated as a controlled or sustained release oral formulation in any suitable tablet, coated tablet or multiparticulate formulation known to those skilled in the art. The sustained release dosage form may optionally include a sustained release carrier which is incorporated into a matrix along with the opioid agonist and opioid antagonist, or may be applied as a sustained release coating.

In embodiments in which the opioid analgesic comprises hydrocodone, the sustained release oral dosage forms may include analgesic doses from about 8 mg to about 50 mg of hydrocodone per dosage unit. In sustained release oral dosage forms where hydromorphone is the therapeutically active opioid, it is included in an amount from about 2 mg to about 64 mg hydromorphone hydrochloride. In another embodiment, the opioid analgesic comprises morphine, and the sustained release oral dosage forms of the present invention include from about 2.5 mg to about 800 mg morphine, by weight. In yet another embodiment, the opioid analgesic comprises oxycodone and the sustained release oral dosage forms include from about 2.5 mg to about 800 mg oxycodone. The opioid analgesic may comprise tramadol and the sustained release oral dosage forms may include from about 25 mg to 800 mg tramadol per dosage unit. The dosage form may contain more than one opioid analgesic to provide a substantially equivalent therapeutic effect. Alternatively, the dosage form may contain molar equivalent amounts of other salts of the opioids useful in the present invention.

In one preferred embodiment of the present invention, the sustained release dosage form comprises such particles containing or comprising the active ingredient, wherein the particles have diameter from about 0.1 mm to about 2.5 mm, preferably from about 0.5 mm to about 2 mm.

The particles are preferably film coated with a material that permits release of the opioid agonist/antagonist combination at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

In certain embodiments, the particles comprise normal release matrixes containing the opioid analgesic with the opioid antagonist.

Coatings

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the opioid in desired areas of the gastrointestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate PVAP), hydroxypropylmethylcellulose phthalate, and methacrylic acid ester copolymers, zein, and the like.

In certain preferred embodiments, the substrate (e.g., tablet core bead, matrix particle) containing the opioid analgesic (with or without the COX-2 inhibitor) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions—are described, e.g., in detail in U.S. Pat. Nos. 5,273,760 and 5,286,493, assigned to the Assignee of the present invention and hereby incorporated by reference.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkycellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate co-polymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragite® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragie® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, 30 however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When a hydrophobic material is used to coat inert pharmaceutical beads such as nu pariel 18/20 beads, a plurality of the resultant solid controlled release beads may thereafter be placed in a gelatin capsule in an amount sufficient to provide an effective controlled release dose when ingested and contacted by an environmental fluid, e.g., gastric fluid or dissolution media.

The controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the hydrophobic material, altering the manner in which the plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethyl-cellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects, drying while the acrylic polymer coating is sprayed on. A sufficient amount of the hydrophobic material to obtain a predetermined controlled release of said therapeutically active agent when the coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in-vitro dissolution rates of the opioid within the preferred ranges and that releases the opioid in a pH-dependent or pH-independent manner. The materials suitable for inclusion in a controlled release matrix will depend on the method used to form the matrix.

For example, a matrix in addition to the opioid analgesic and (optionally) COX-2 may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts (or softens to the extent necessary to be extruded) may be used in accordance with the present invention.

Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid allylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 300 to about 200° C., preferably from about 45° to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30° to about 100° C.

Suitable hydrophobic materials which may be used in accordance with the present invention include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylehe glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/ polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

Processes for Preparing Matrix-Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opioid or an opioid salt; (b) mixing the hydroxyalkyl cellulose containing granules with at least one $C_{12}$–$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such-embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate co-polymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598, assigned to the Assignee of the present invention and hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

Melt Extrusion Multiparticulates

The preparation of a suitable melt-extruded matrix according to the present invention may, for example, include the steps of blending the opioid analgesic, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate (s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553–1593 (1980), incorporated by reference herein.

In yet another preferred embodiment, the extrudate can be shaped into tablets as set forth in U.S. Pat. No. 4,957,681 (Klimesch, et. al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opioid analgesic compound utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the therapeutically active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/ or the retardant material.

DETAILED DESCRIPTION OF PREFERRED EMBODIMENTS

The following examples illustrate various aspects of the present invention. They are not to be construed to limit the claims in any manner whatsoever.

A direct comparison of the competitive antagonist properties of naltrexone following its coadministration with various opioid agonists has not been undertaken previous to the present invention, to the knowledge of the inventors. However, dose-ranging studies have been conducted evaluating the opioid antagonist properties in subjects receiving either heroin or morphine challenges. In general, preadministration of naltrexone 50 mg 24 hours prior to 25 mg of intravenous heroin challenge completely blocked or attenuated the opioid agonist effects. See, Gonzalez J P, Broden R N. "Naltrexone: A Review of its Pharmacodynamic and Pharmacokinetic Properties and Therapeutic Efficacy in the Management of Opioid Dependence." *Drugs* 1988; 35:192–213; Resnick R R, Valavka J, Freedman A M, Thomas M. "Studies of EN-1639A (Naltrexone): A New Narcotic Antagonist." *Am. J. Psychiatry* 1974; 131:646–650, both of which are hereby incorporated by reference.

EXAMPLE 1

In Example 1, a randomized, single-blind, placebo-controlled, single-dose, four-way crossover study was conducted which assessed whether naltrexone oral solution 6.4 mg would block opioid agonist properties of hydrocodone 15 mg in 6 normal, healthy, female volunteers. The study population included only females because previous observations have indicated that females have an increased sensitivity to the opioid agonist effects as compared to males. The four treatments were HYIR/APAP (2 tablets of hydrocodone 7.5 and acetaminophen 750 mg, Vicodin ES®) and naltrexone oral solution 3.2 mg, HYIR/APAP (2×7.5 mg) and naltrexone oral solution 6.4 mg, HYIR comparator tablets (2×750 mg Trilisate® tablets) and naltrexone oral solution (placebo), and HYIR/APAP (2 tablets of Vicodin ES®) and naltrexone oral solution (placebo). All treatments were administered under fasted conditions. A 48-hour washout period occurred between doses. Subjects were randomly assigned to four treatment sequences of the four treatment groups. Subjects reported to the testing facility the evening prior to the first dose and remained confined there until completion of the 24-hour post-dose assessment of the last dose. Safety measurements consisted of reports of adverse events, vital signs, abnormal laboratory values, abnormal physical examination and ECG results. Pharmacodynamic parameters (pupil size and Modified Specific Drug Effect Questionnaire) were also assessed.

Test Treatments

The four treatments were as follows:

Hydrocodone immediate-release tablets (2×7.5 mg) and naltrexone oral solution 3.2 mg.

Hydrocodone immediate-release tablets (2×7.5 mg) and naltrexone oral solution 6.4 mg.

Hydrocodone immediate-release comparator tablets and placebo naltrexone oral solution.

Placebo hydrocodone immediate-release tablets (2×7.5 mg) and placebo naltrexone oral solution.

Test Products

The products evaluated in this study include Vicodin ES® (hydrocodone bitartrate 7.5 mg and acetaminophen 750 mg, Knoll Pharmaceuticals), Trilisate® (choline magnesium trisalicylate 750 mg, Purdue Frederick) which served as the comparator, and naltrexone powder. Vicodin ES® was selected as the active treatment since the acetaminophen portion within this product is expected to have no effect on the central nervous system or pupillary measurement. Trilisate was selected to be used as the "comparator" since its physical appearance is similar to Vicodin ES® and it has no effect on the central nervous system or pupillary measurement. Naltrexone powder formulation was selected rather than the commercially approved tablet formulation (Revia® 50 mg tablets, DuPont) to improve the overall precision in the preparation of the oral solution. An on-site research pharmacist reconstituted the oral solution from the naltrexone powder in a sterile environment utilizing appropriate pharmaceutical techniques. Naltrexone powder (Mallinckrodt Chemical) was used to formulate the naltrexone solution. Individual stock solutions of naltrexone were prepared using a modification of the method proposed by Tsang and Holtsman. Tsang B K, Holtsman R. "Room Temperature Stability of Liquid Naltrexone." *Anesthesiology* 1995:83:A864, hereby incorporated by reference. Immediately prior (<60 minutes) to each dosing period, a naltrexone stock solution was prepared by weighing out 32 mg and 64 mg of naltrexone powder. Each of these portions was dissolved in 50 mL of distilled water and 50 mL of simple syrup, NF for a vinal volume of 100 mL. The concentration of the final solutions was 0.32 mg/mL (32 mg/100 mL) and 0.64 mg/mL (64 mg/100 mL), respectively. These concentrations allowed the same volume (10 mL) of naltrexone oral solution to be administered during each dosing period. The naltrexone oral solution placebo was prepared in the same vehicle as the active solution. The addition of a bittering agent, Bitterguard (denatonium benzoate, NF) powder, was added to provide a taste similar to the active solution.

Pharmacodynamic Measurements a. Pupil Size—Measured by Pupillometry

Pupillary diameter measurements were made with the Polaroid CU-5 camera with a 75 mm lens and built-in electronic ring flash using Polacolor ER 669 instant pack film.12. This method has become accepted as a safe and accurate way to study pupils and is commonly regarded as being second only to the infrared television pupillometric technique (a more versatile and sophisticated, but also much more expensive and cumbersome, method). The Polaroid CU-5 method is said to be accurate to within 0.1 millimeters. See, Czarnecki J S, Pilley S F, Thompson H S. "The Use of Photography in the Clinical Evaluation of Unequal Pupils." *Canad J Ophthal* 1979;14:297–302; hereby incorporated by reference.

Pupil diameters were measured as follows: The camera was modified by covering two small sections of the ring flash at 3 and 9 o'clock so that the corneal reflection of the flash does not obscure the horizontal pupillary margin. The camera was centered in front of the subject's face with 3 inch frame against the lateral orbital rims and the eyes occupying the very top of the field (to minimize upgaze). The subject was asked to look just over the camera body and to fixate on a non-accommodative target in the distance, thereby minimizing the near reflex. With the volunteer fixing in the distance, the photo was taken. All photographs were taken in constant ambient light. The pupillary latency was such that the flash will not affect pupillary diameter. Tonic constriction of the pupil after the flash does occur, but is of short duration; therefore, it did not interfere with the measurements necessary for this trial. See, Smith S A, Dewhist R R. "A Single Diagnostic Test for Pupillary Abnormality in Diabetic Autonomic Neuropathy." *Diabetic Medicine* 1988;3:38–41; hereby incorporated by reference. Development of the print for the recommended length of time (approximately one (1) minute, varying with ambient temperature) will produce a one-to-one photograph of the volunteer's midface, with the pupils at the top of the print. Horizontal pupillary diameter is then measured using a simple plus magnifier with a built-in reticule calibrated to 0.1 millimeter. Only the left eye was used to measure pupillary effects at each time period specified in the protocol.

b. A Modified Specific Drug Effect Questionnaire.

The questionnaire is a modification of the 22 item questionnaire used by Jasinski and Preston. See, Jasinski D R. "Assessment of the Abuse Potential of Morphine-Like Drugs (methods used in man)." In:*Drug Addiction I* (Martin, W. R., ed.), 1997:197–258. Springer-Verlag, New York; Preson K L, Jasinski D R, Testa M. "Abuse Potential and Pharmacological Comparison of Tramadol and Morphine." *Drug and Alcohol Dependence* 1991;27:7–17; both of which are hereby incorporated by reference. The present questionnaire consisted of 10 items rated by the subject 10 minutes prior to blood sampling. The item is related to signs of opiate agonist drugs and was as follows:

Subject questions: 1) do you feel any effects from the drugs?, 2) does your skin feel itchy?, 3) do you feel relaxed?, 4) do you feel sleepy?, 5) do you feel drunk?, 6) do you feel nervous?, 7) do you feel full of energy?, 8) do you feel you need to talk?, 9) do you feel sick to your stomach?, 10) do you feel dizzy? The subject then rated the item by placing a vertical mark along a 100 mm visual analog scale (VAS) anchored on one end by "not at all" and at the other end by "an awful lot".

Pupil size of the left eye made at baseline (within 30 minutes prior to dosing), and at 0.5, 1, 2, 4, 6, 9 and 12 hours post-dose was measured, and the subject rated drug effect scores as measured on a visual analog scale for the Modified Specified Drug Effect Questionnaire ("MSDEQ") at baseline, and at 0.5, 1, 2, 4, 6, 9 and 12 hours post-dose.

Separate graphs for the eleven responses (NSDEQ questions and pupillary diameter measurement) versus naltrexone dose were visually and statistically examined to determine the nominally effective dose of naltrexone in combination with the hydrocodone dose used in the study.

The adverse events reported were those commonly associated with the administration of opioid analgesics, and most were classified as "mild". No serious adverse events or deaths occurred, and no patients were discontinued from the study secondary to adverse events.

Figure 2:
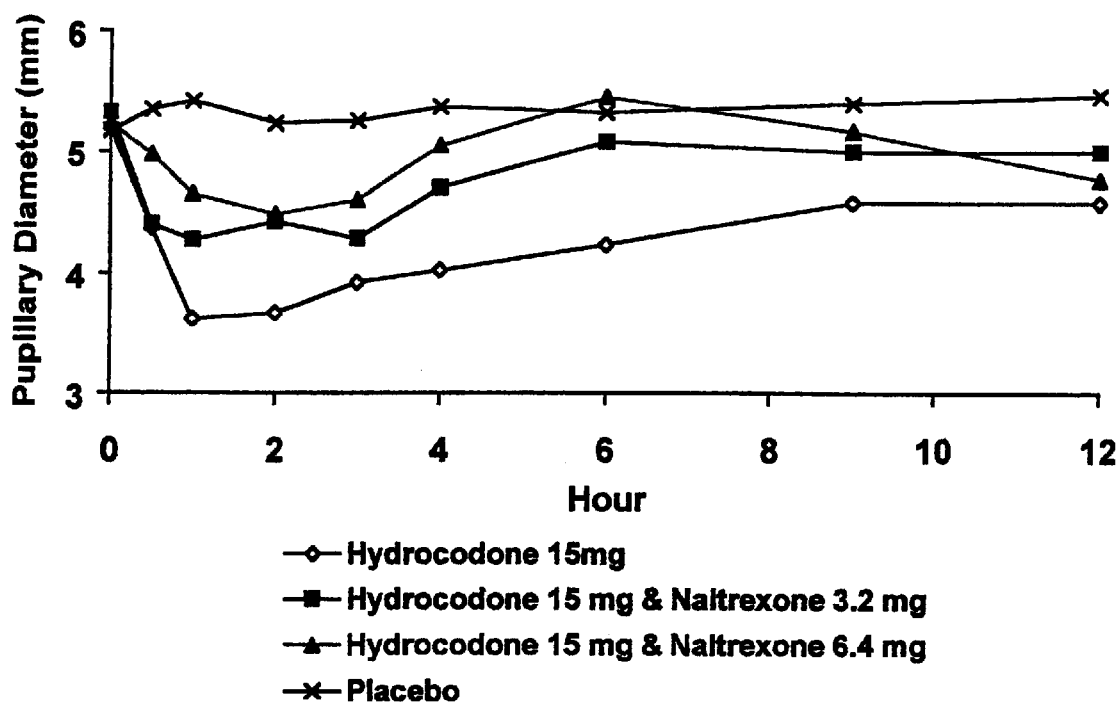
FIG. 2 presents the naltrexone antagonism of hydrocodone-induced pupillary constriction for Example 1.

Results are presented in FIGS. 1 and 2.

FIG. 1 shows the naltrexone antagonism of hydrocodone-induced VAS (Visual Analog Scale) "drug effect". This refers to the first question of the Modified Specific Drug Effect Questionnaire which asked the subjects "do you feel any effects of the drug?". The results suggest that there is a dose-response effect for naltrexone; increasing the dose of naltrexone decreased the VAS "drug effect" of hydrocodone. The 6.4-mg dose of naltrexone antagonized the effects of a 15-mg dose of hydrocodone to a greater degree than the 3.2-mg naltrexone dose. The opioid effect of hydrocodone was not completely blocked by the 6.4-mg naltrexone dose.

FIG. 2 shows the naltrexone antagonism of hydrocodone-induced pupillary constriction. These results also suggest a dose-response effect for naltrexone; increasing the dose of naltrexone caused less pupillary constriction in subjects who had received hydrocodone 15 mg. The 6.4-mg naltrexone dose antagonized hydrocodone-induced pupillary constriction to a greater degree than the 3.2-mg naltrexone dose. The pupillary constriction of hydrocodone was not completely blocked by the 6.4-mg naltrexone dose. The least amount of pupillary constriction occurred in the placebo-group. The hydrocodone plus naltrexone placebo-group experienced the most pupillary constriction, and therefore, had the lowest measurements for pupillary diameter.

EXAMPLE 2

In Example 2, a ten period, randomized, crossover, single-blind study evaluating the ratio of oral naltrexone to oral hydrocodone that would nominally minimize the opioid agonist effects was conducted in normal, healthy, female volunteers. Twenty-one subjects enrolled in the study, and 16 completed the study. The ten treatments included HYIR/APAP (2 tablets of hydrocodone 7.5 and acetaminophen 750 mg per tablet, Vicodin ES®) with the following doses of naltrexone oral solution: 0.4 mg/10 mL, 0.8 mg/10 mL, 1.6 mg/10 mL, 3.2 mg/10 mL, 4.8 mg/10 mL, 6.4 mg/10 mL, 9.6 mg/10 mL, 12.8 mg/10 mL, and placebo naltrexone oral solution, as well as hydrocodone immediate-release comparator tablets (2×750 mg Trilisate® tablets) with placebo naltrexone oral solution. All treatments were administered under fasted conditions. A 48-hour washout period occurred between doses. Subjects were randomly assigned to ten treatment sequences of the ten treatment groups. Subjects reported to the testing facility the evening prior to the first dose and remained confined there until completion of the 24-hour post-dose assessment of the last dose. Safety measurements consisted of reports of adverse events, vital signs, abnormal laboratory values, abnormal physical examination and ECG results. Plasma hydrocodone, naltrexone and 6-β-naltrexol levels were obtained, and pharmacokinetic values will be calculated and analyzed. Pharmacodynamic parameters (pupil size and Modified Specific Drug Effect Questionnaire) were also assessed.

Dosing Regimen

The dosing regimen was as follows:

Hydrocodone immediate-release comparator (placebo) tablets were administered with 10 mL naltrexone oral solution (placebo) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (placebo) at approximately 08:00 on the dosing day in Periods I through 10 following an 8-hour fast. The fast continued for an additional four (4) hours post-dose;

Hydrocodone immediate-release tablets (2×7.5 mg) were administered with 10 mL naltrexone oral solution (0.4 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (0.8 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (1.6 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (3.2 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (4.8 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (6.4 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (9.6 mg) at approximately 08:00 on the dosing day in Periods 1 through 10 following an 8-hour fast. The fast continued for an additional four (4) hours post-dose;

Hydrocodone immediate-release tablets (2×7.5 mg) were administered with 10 mL naltrexone oral solution (12.8 mg) at approximately 08:00 on the dosing day in Periods 1 through 10 following an 8-hour fast. The fast continued for an additional four (4) hours post-dose.

The subjects observed an 8 hour fast preceding and fasted for four (4) hours following each dose administration of the assigned drug on each dosing day. A baseline blood sample (for Plasma Hydrocodone, Naltrexone and 6-β-naltrexol) was obtained prior to dosing (within 30 minutes) administration of initial dose (0 hr) and at 0.5, 1, 2, 4, 6 and 9 hours post-dose. All samples were collected within ± 2 minute of the scheduled time. Measurements of the following pharmacodynamic parameters were made just prior to blood sampling at baseline (within 30 minutes prior to dosing), and at 0.5 hr, 1 hr, 2 hr, 4 hr, 6 hr and 9 hr post-dose.

Immediately prior to each dosing period, 8 individual naltrexone stock solutions were prepared by weighing out 4, 8, 16, 32, 48, 64, 96, and 128 mg of naltrexone powder. Each of these portions were dissolved in 50 ml of distilled water and 50 ml of simple syrup. The final solution was 100 mL at a concentration of 0.04, 0.08, 0.16, 0.32, 0.48, 0.96, and 1.28 mg/mL. These concentrations allowed the same volume (10 ml) of naltrexone solution to be administered during each dosing period. The naltrexone placebo solution was be prepared in the same vehicles as the active solution. The addition of a bittering agent, Bitterguard Powder (denatonium benzoate), was added to provide a taste similar to the active solution.

Pharmacodynamic Measurements

Pharmacodynamic measurements for Example 2 were obtained in accordance with the procedures set forth with respect to Example 1 above.

Figure 3:
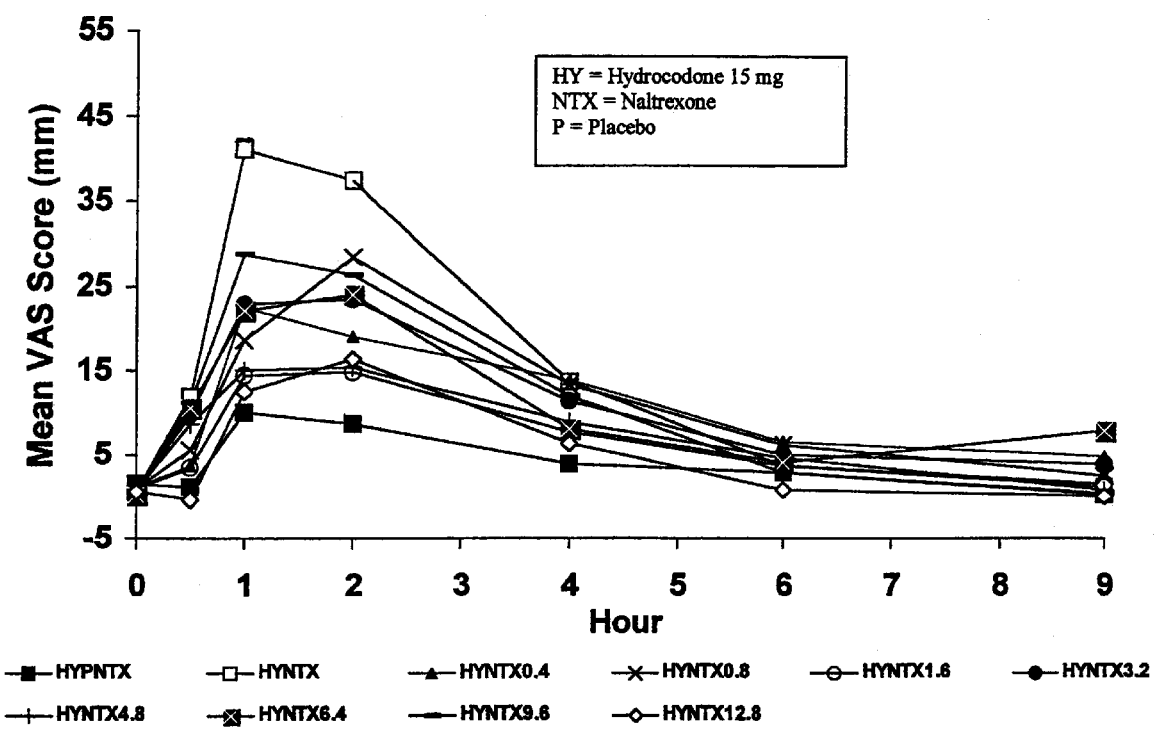
FIG. 3 presents the mean "drag effect" VAS score over time for each of the treatments of Example 2.
Figure 4:
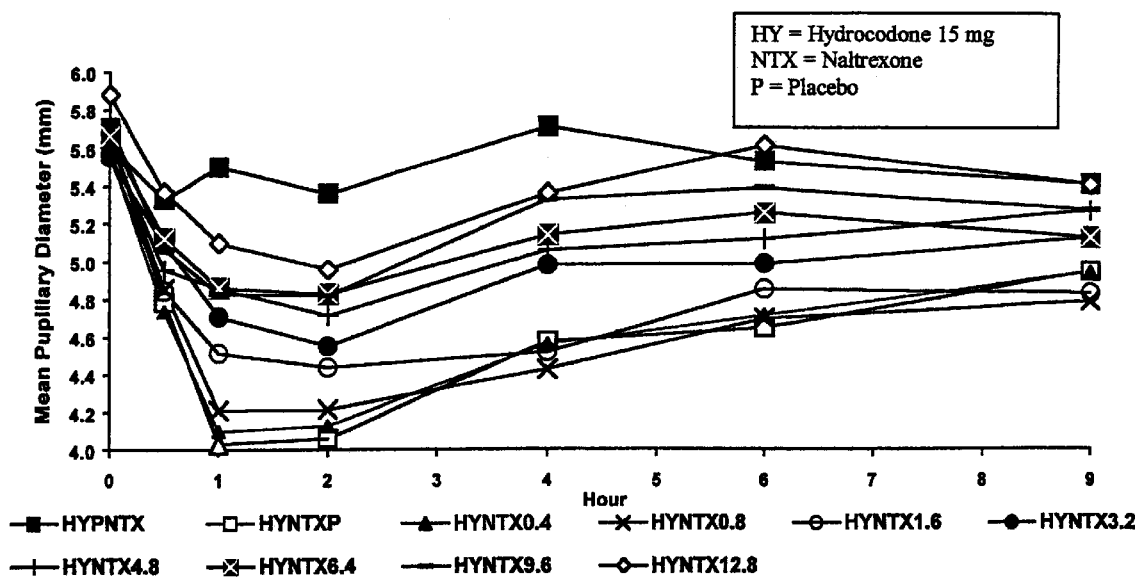
FIG. 4 presents the mean "drug effect" pupil diameters over time for each of the treatments of Example 2.
Figure 5:
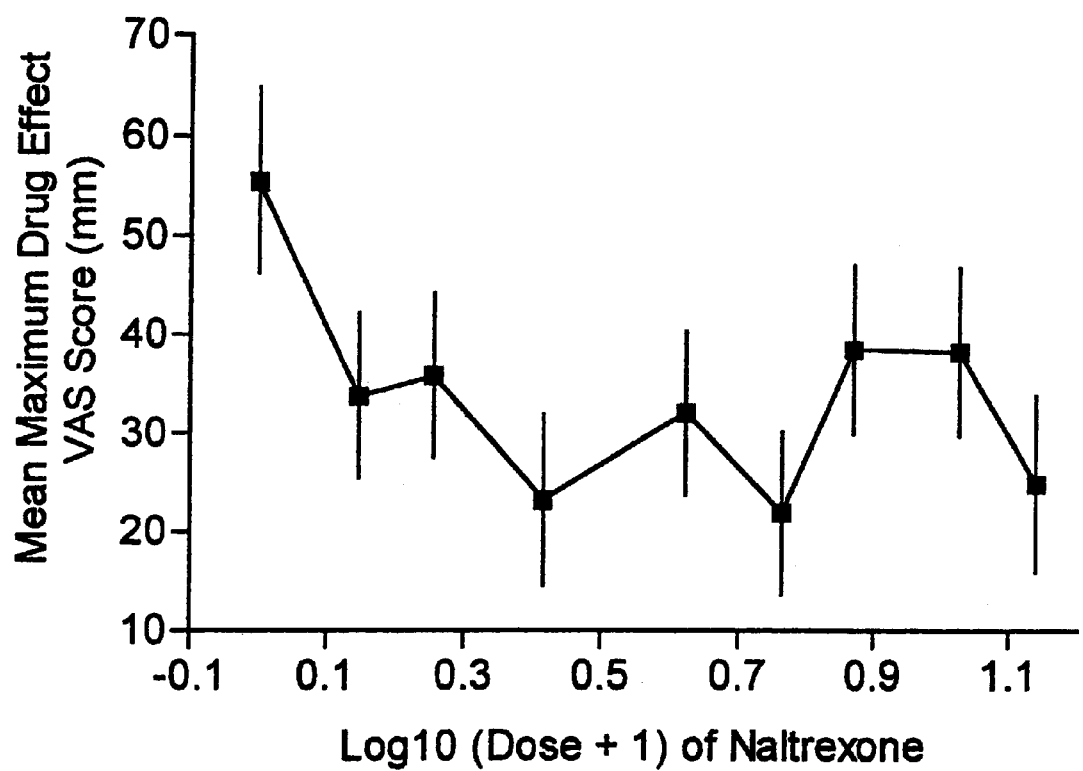
FIGS. 5 and 6 present the corresponding mean maximum "drug effect" VAS score (±95% CI) and mean minimum pupil diameter (±95% CI) versus the log from each of the naltrexone doses of Example 2.
Figure 6:
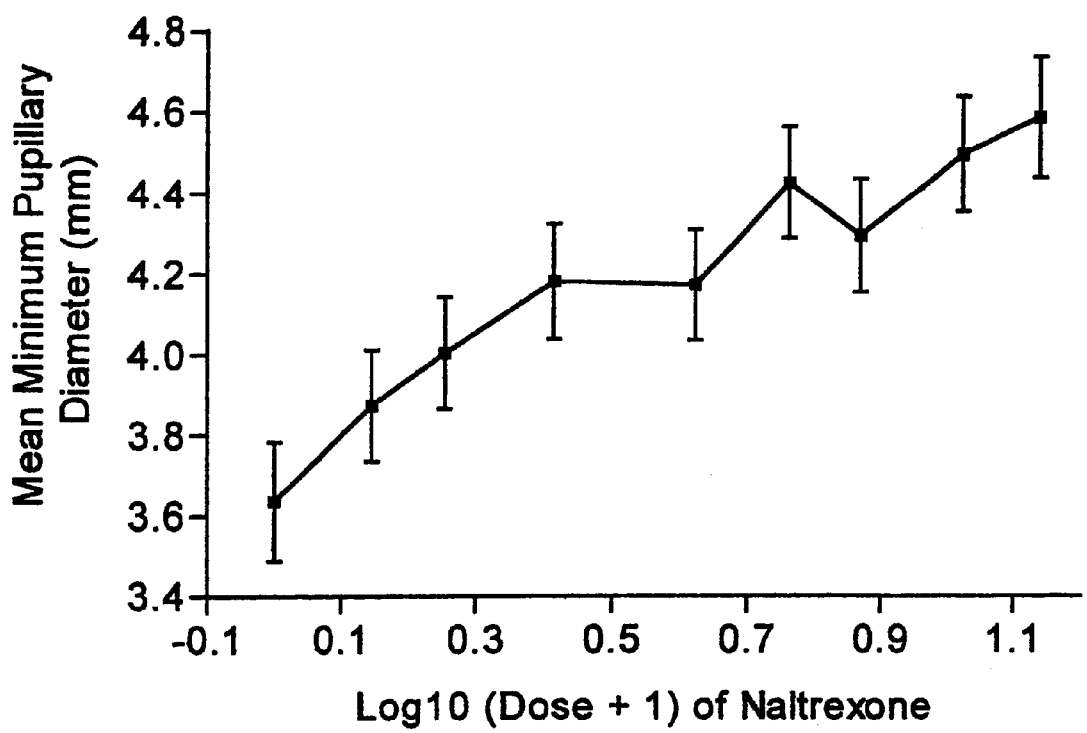

The mean "drug effect" VAS score and pupil diameter over time for each of the treatments are presented in FIGS. 3 and 4, respectively. In general, the single-dose administration of hydrocodone immediate release/ acetaminophen ("HYIR/APAP") with increasing doses of naltrexone (range 0 mg–12.8 mg) resulted in an overall decrease in "drug effect" VAS score and decrease in pupillary constriction. FIGS. 5 and 6 present the corresponding mean maximum "drug effect" VAS score (±95% CI) and mean minimum pupil diameter (±95% CI) versus the log from each of the naltrexone doses. Both figures suggest a dose-response relationship with the pupil effect demonstrating a greater dose-response relationship compared to the "drug effect" VAS response.

The results suggest that even with the inclusion of 0.4 mg naltrexone, there was a diminution of pharmacologic effects of the dose of hydrocodone. Approximately 0.4 mg of naltrexone minimally antagonized the 15 mg hydrocodone dose. Dosages above naltrexone 0.4 mg began to show increasing diminution of the effect of the hydrocodone dose.

The adverse events reported were those commonly associated with the administration of opioid analgesics, and most were classified as "mild". A total of five subjects (5/21) discontinued the study. Three subjects discontinued due to adverse events. Two of these subjects experienced adverse events which were classified as non-serious. One subject developed anemia which was classified as serious, and required iron therapy. Another two subjects were discontinued from the study because their physicians felt there was information in their medical history that did not make it possible for them to participate. No deaths occurred in this study.

In general, the single-dose administration of 15 mg hydrocodone immediate-release tablets with increasing doses of naltrexone oral solution (range 0 mg –12.8 mg) resulted in an overall decrease in "drug effect" VAS score and an increase in pupil diameter.

EXAMPLE 3

Example 3 presents the results of a study evaluating precipitated withdrawal in morphine dependent volunteers receiving hydrocodone immediate-release tablets and naltrexone oral solution. The study was a single-blind, single-dose, placebo-controlled naltrexone dose ascending study in subjects physically dependent on opioids. The experimental subjects (5) were opioid-dependent as determined by Narcan challenge, Addiction Severity Index scores, physical examination, observation and urine drug screen results, and were not currently seeking treatment for their addiction. To evaluate precipitated withdrawal following the coadministration of hydrocodone immediate release and naltrexone, a 30 mg dose of hydrocodone immediate release was selected to simulate a dose level used by individuals who abuse hydrocodone. This is also a dose which is considered to be equianalgesic to other commonly used opioids in opioid naive patients. The relative analgesic potency of hydrocodone is believed to be similar to that of oxycodone and about two times that of oral morphine.

Test Treatments

The treatments were as follows:

Hydrocodone/acetaminophen immediate-release (HYIR/APAP) tablets 30 mg (Lortab® 3×10 mg) and increasing doses of naltrexone oral solutions 0, 0.25 mg, 0.5 mg, 1.0 mg and 2.0 mg. Hydrocodone/acetaminophen immediate-release (HYIR/APAP) tablets 30 mg (Lortab® 3×10 mg) and naltrexone placebo oral solution. The naltrexone oral solution and placebo solution were prepared in accordance with Examples 1–2.

The subjects were stabilized for 5 days by administering 15 mg morphine sulphate i.m. at regular intervals: 6 and 10 A.M., and 4 and 10 P.M. daily. Fifteen mg morphine sulphate i.m. is equivalent to 30 mg hydrocodone given orally. The study medications were administered after stabilization at 10 AM on study medication dosing days, and observations were made over the next six hours. After six hours, if precipitated withdrawal was not observed, the administration of morphine sulfate 15 mg intramuscularly resumed with the 4 PM dose. The subjects were stabilized 48 hours before the next study drug administration. Following each treatment (1–4), if precipitated withdrawal was not observed, the subject received study medication from the next treatment in the following ascending order:

Treatment No. 1: HYIR/APAP tablets 30 mg (Lortab® 3×10 mg) administered with placebo naltrexone (10 mL) oral solution at approximately 10:00 on the dosing day following an 8-hour fast. The fast continued for an additional four (4) hours post-dose.

Treatment No. 2: HYIR/APAP tablets 30 mg (Lortab® 3×10 mg) administered with 0.25 mg naltrexone (10 mL) oral solution at approximately 10:00 on the dosing day following an 8-hour fast. The fast continued for an additional four (4) hours post-dose.

Treatment No. 3: HYIR/APAP tablets 30 mg (Lortab® 3×10 mg) administered with 0.5 mg naltrexone (10 mL) oral solution at approximately 10:00 on the dosing day following an 8-hour fast. The fast continued for an additional four (4) hours post-dose.

Treatment No. 4: HYIR/APAP tablets 30 mg (Lortab® 3×10 mg) administered with 1.0 mg naltrexone (10 mL) oral solution at approximately 10:00 on the dosing day following an 8-hour fast. The fast continued for an additional four (4) hours post-dose.

Treatment No. 5: HYIR/APAP tablets 30 mg (Lortab® 3×10 mg) administered with 2.0 mg naltrexone (10 mL) oral solution at approximately 10:00 on the dosing day following an 8-hour fast. The fast continued for an additional four (4) hours post-dose.

Blood samples were collected at 0.5 hours pre-dose, and at 0.5, 1, 2, 4 and 6 hours post-dose. Pupil diameter measurements were obtained using a Pupilscan pupillometer and recorded in millimeters to the nearest millimeter. There was a 48 hour washout period following each test period. Four subjects completed the study, one subject was terminated. The effect of naltrexone was a slight abstinence (symptoms of withdrawal) at 1 and 2 mg.

The protocol was amended and twelve experimental subjects participated in the protocol, which was identical to the study outlined above except for the increased ratio of naltrexone. Naltrexone doses in the revised protocol were 0, 1, 2, 4 and 8 mg. Eight of the experimental subjects completed the study, while four withdrew.

Vital signs for each subject were monitored, and subjects were monitored for signs and symptoms of opioid withdrawal. Withdrawal signs include stuffiness or running nose, tearing, yawning, sweating, tremors, vomiting, piloerection, mydriasis, irritability and restlessness. Withdrawal symptoms include feeling of temperature change, joint, bone or muscle pain, abdominal cramps, skin crawling, nausea, and the subject's reporting the subjective experience of the aforementioned symptoms.

To provide a measure of the subjective experience of the drug combination, the subjects answered questionnaires throughout the study period. The responses to questions were graded on the Visual Analog Scale as described in Example 1. The subjective experiences that were assessed were as follows: like/dislike of the drug, ability to perceive drug effect, sweating, restlessness, shakiness, watery eyes, gooseflesh, stomach upset, nasal congestion, sleepiness, cold, hot, muscle ache, tenseness or relaxation, confusion, fearfulness, irritability, talkativeness, sensations of withdrawal, sensations of sickness. The subjects were also observed for the following symptoms: yawning, scratching, relaxed, nasal congestion, irritability, withdrawal. In addition, blood pressure, pulse rate, respiration rate, pupil size and body temperature were monitored.

The data for five of the subjects are presented below. FIGS. 7A–C illustrate the mean scores for subjective perception of hydrocodone from the questionnaires, plotted as a function of time post administration and as a function of naltrexone dose. FIG. 7A illustrates the subjects' ability to feel the effect of hydrocodone in the presence of varying amounts of naltrexone. FIGS. 7B and 7C illustrate the subjects'favorable or unfavorable subjective experiences of hydrocodone in the presence of varying amounts of naltrexone, respectively.

Figure 8A:
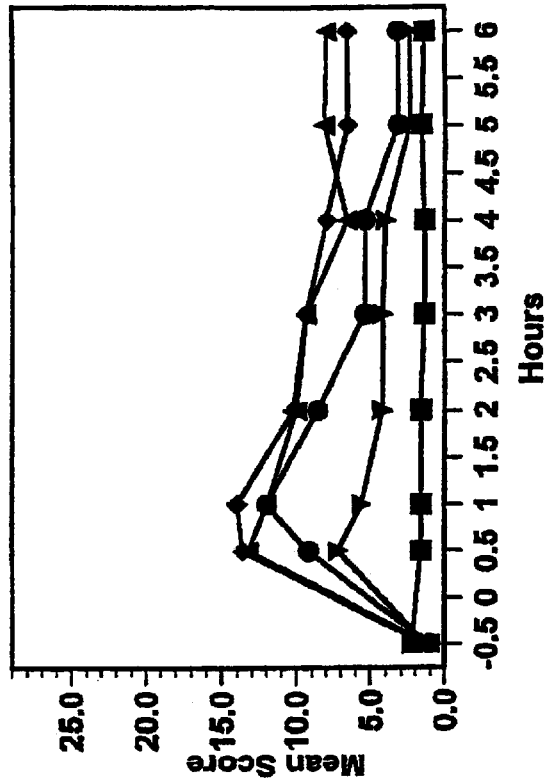
FIG. 8A illustrates the subjects' perception of withdrawal from the effect of hydrocodone in the presence of varying amounts of naltrexone in Example 3.
Figure 8B:
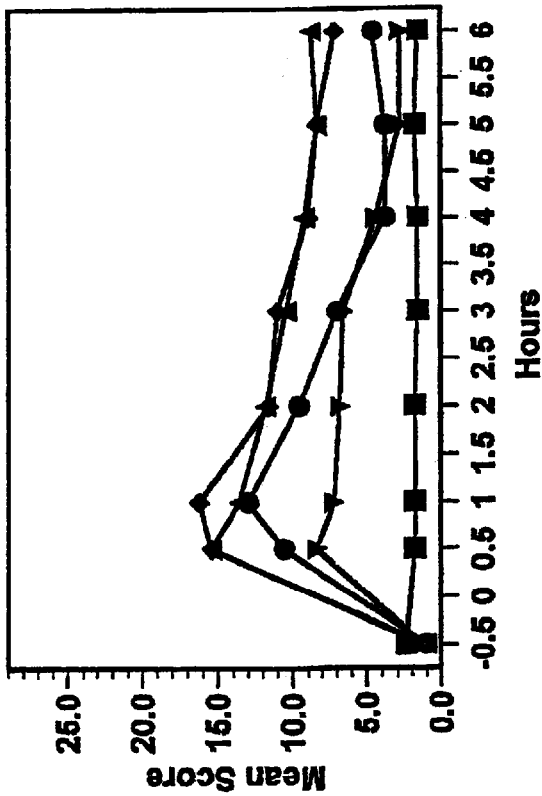
FIG. 8B illustrates the subjective experience of illness in the presence of varying amounts of naltrexone in Example 3.

FIGS. 8A and B illustrate the mean scores for subjective perception of the effects of hydrocodone, plotted as a function of time post administration and as a function of naltrexone dose. FIG. 8A illustrates the subjects' perception of withdrawal from the effect of hydrocodone in the presence of varying amounts of naltrexone. FIG. 8B illustrates the subjective experience of illness in the presence of varying amounts of naltrexone. FIG. 9A illustrates the effect on pupil size of hydrocodone in the presence of varying amounts of naltrexone. FIG. 9B illustrates the apparent extent of withdrawal from the effect of hydrocodone in the presence of varying amounts of naltrexone, from the perspective of the observer.

Figure 10B:
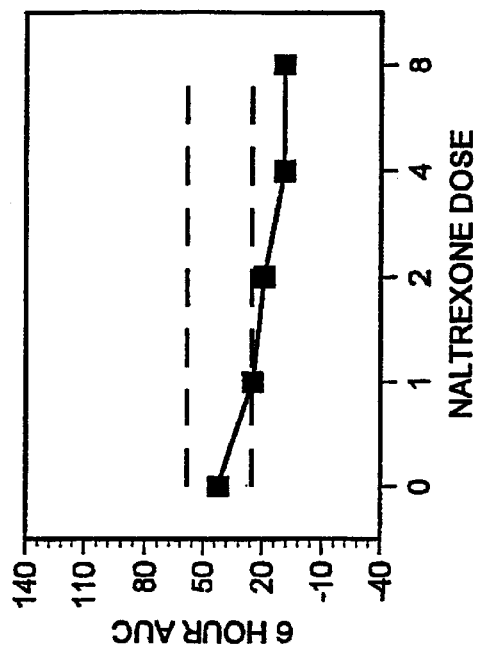
FIGS. 10A–C present the areas under the curves presented in FIGS. 7A–C, integrated over the 6 hour observation period, as a function of naltrexone dose, and the 95% confidence levels for the placebo response of naltrexone (30 mg hydrocodone, 0 mg naltrexone)
Figure 10C:
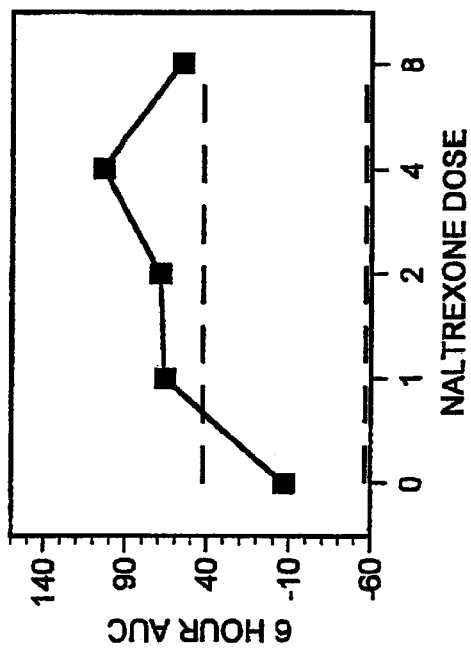
Figure 10A:
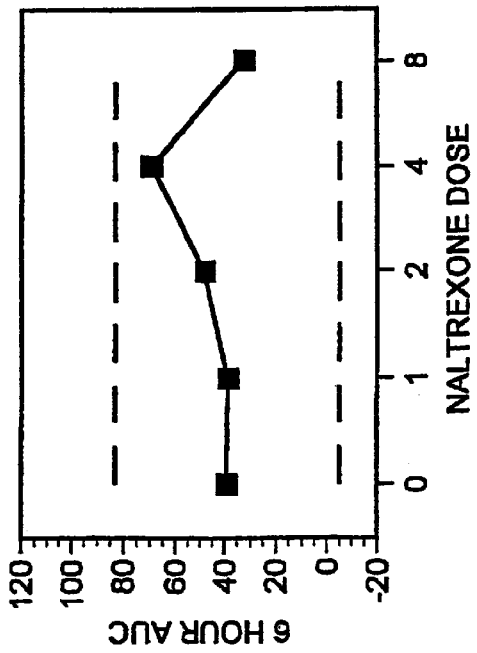

FIGS. 10A–C present the areas under the curves presented in FIGS. 7A–C, integrated over the 6 hour observation period, as a function of naltrexone dose, and the 95% confidence levels for the placebo response of naltrexone (30 mg hydrocodone, 0 mg naltrexone). FIG. 10A illustrates that up to 8 mg naltrexone does not abolish the ability of the subject to perceive the effect of hydrocodone: the experimentally determined AUC (0 to 6 hours) observed for each naltrexone dose lies wholly within the 95% confidence limits for the naltrexone placebo response. FIG. 10B illustrates the AUC (0 to 6 hours) for the subjects' favorable subjective experience to hydrocodone as a function of naltrexone dose. FIG. 10B illustrates that the favorable subjective experience is decreased for>1 mg naltrexone, that is, the experimentally determined AUC (0 to 6 hours) decreased below the 95% confidence limits for naltrexone placebo at approximately 1 mg naltrexone. FIG. 10C illustrates that the unfavorable subjective experience is increased for>1 mg naltrexone, that is, the experimentally determined AUC (0 to 6 hours) increased above the 95% confidence limits for naltrexone placebo at approximately 1 mg naltrexone.

Figure 11A:
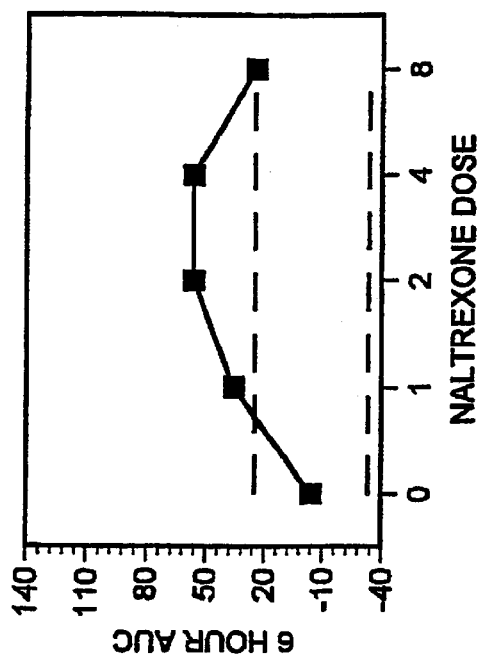
FIGS. 11A–C present the areas under the curves presented in FIG. 8A–B and FIG. 9A, integrated over the 6 hour observation period, as a function of naltrexone dose, and the 95% confidence levels for the placebo response of naltrexone (30 mg hydrocodone, 0 mg naltrexone).
Figure 11B:
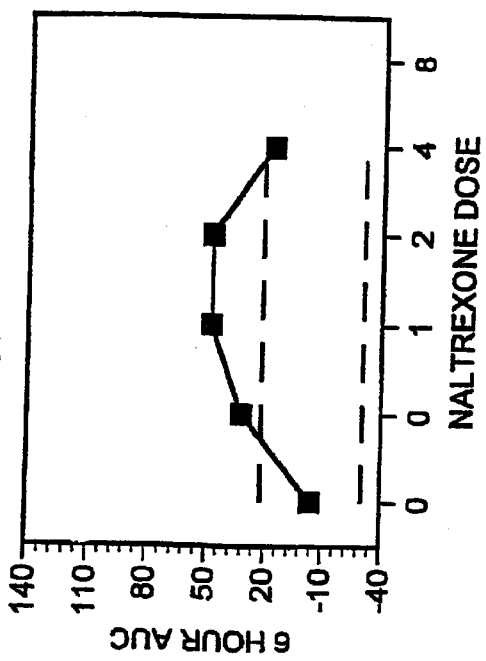
Figure 11C:
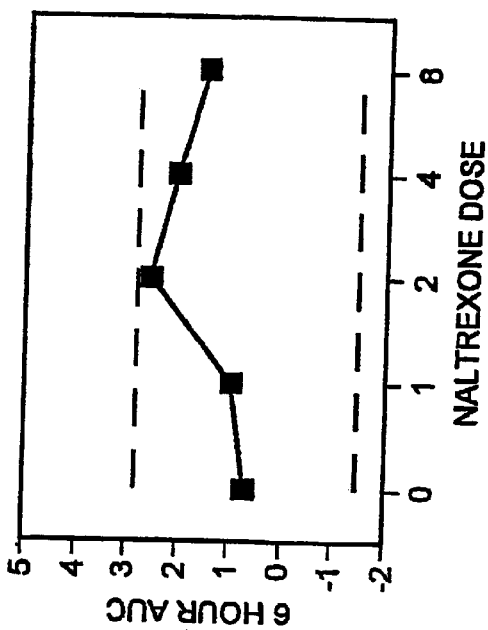

FIGS. 11A–C present the areas under the curves presented in FIGS. 8A-B and FIG. 9A, integrated over the 6 hour observation period, as a function of naltrexone dose, and the 95% confidence levels for the placebo response of naltrexone (30 mg hydrocodone, 0 mg naltrexone). FIG. 11A illustrates the AUC (0 to 6 hours) for the subjective experience of illness in the presence of varying amounts of naltrexone. FIG. 11A demonstrates that doses of naltrexone greater than approximately 0.75 mg result in the subjective experience of withdrawal: the experimentally determined AUC (0 to 6 hours) observed in FIG. 8A for each naltrexone dose increases above the 95% confidence limits for the naltrexone placebo response at approximately 0.75 mg naltrexone. FIG. 11B illustrates the AUC (0 to 6 hours) for the subjects' perception of illness in the presence of varying amounts of naltrexone. FIG. 11B demonstrates that doses of naltrexone greater than approximately 0.75 mg result in the subjective experience of illness: the experimentally determined AUC (0 to 6 hours) observed in FIG. 8B for each naltrexone dose increases above the 95% confidence limits for the naltrexone placebo response at approximately 0.75 mg naltrexone. FIG. 11C illustrates the AUC (0 to 6 hours) of the experimentally determined change in pupil size as a function of naltrexone dose. FIG. 11C demonstrates that up to 8 mg naltrexone does not abolish the miosis effect of hydrocodone: the experimentally determined AUC (0 to 6 hours) observed in FIG. 9A for each naltrexone dose lies wholly within the 95% confidence limits for the naltrexone placebo response.

The clinical study demonstrates that hydrocodone, in combination with naltrexone, has an onset of <0.5 hours, peaks within 0.5 to 1 hour and is markedly diminished within 3 to 4 hours. A shallow dose-response curve was observed. The addition of naltrexone decreased the favorable subjective experience of hydrocodone, increased the subjective experience of dislike for hydrocodone and increased the subjective experience of sickness and withdrawal from the effects of hydrocodone. These experiences are clearly aversive.

While the invention has been described and illustrated with reference to certain preferred embodiments thereof, those skilled in the art will appreciate that obvious modifications can be made herein without departing from the spirit and scope of the invention. Such variations are contemplated to be within the scope of the appended claims.

What is claimed is:

1. An oral dosage form, comprising an orally therapeutically effective dose of an opioid agonist, and an opioid antagonist, the dosage form having a ratio of opioid antagonist to opioid agonist that provides a combination product which is analgesically effective when the combination is administered orally, but which (i) is aversive in physically dependent human subjects when administered at the same dose as said therapeutically effective dose; and (ii) maintains an analgesic effect but does not increase analgesic efficacy of the opioid agonist relative to the same therapeutic dose of opioid analgesic when administered to human patients without said opioid antagonist.

2. The oral dosage form of claim 1, wherein the amount of antagonist included in the oral dosage form causes an aversive experience in a physically dependent addict taking about 2–3 times the usually prescribed dose of the opioid.

3. The oral dosage form of claim 1, wherein the opioid agonist is hydrocodone and the antagonist is naltrexone.

4. The oral dosage form of claim 3, wherein the ratio of naltrexone to hydrocodone is from about 0.03:1 to about 0.27:1.

5. The oral dosage form of claim 3, wherein the ratio of naltrexone to hydrocodone is from about 0.05:1 to about 0.20:1.

6. The oral dosage form of claim 1, wherein the opioid agonist or analgesic is selected from the group consisting of morphine, hydromorphine, hydrocodone, oxycodone, codeine, levorphanol, meperidine, methadone, and mixtures thereof.

7. The oral dosage form of claim 1, further comprising an additional non-opioid drug selected from the group consisting of an NSAID, a COX-2 inhibitor, acetaminophen, aspirin, an NMDA receptor antagonist, a drug that blocks a major intracellular consequence of NMDA-receptor activation, an antitussive, an expectorant, a decongestant, an antihistamine and mixtures thereof.

8. The oral dosage form of claim 1, further comprising one or more pharmaceutically acceptable inert excipients.

9. The oral dosage form of claim 6, wherein said opioid antagonist is selected from the group consisting of naltrexone, naloxone, nalmephene, cyclazocine, levallorphan, and mixtures thereof.

10. The oral dosage form of claim 6, wherein said opioid antagonist is naltrexone.

11. The oral dosage form of claim 1, further comprising a sustained release carrier which imparts sustained release properties to said opioid agonist.

12. The oral dosage form of claim 1, wherein said opioid antagonist is naltrexone and said opioid agonist is oxycodone, wherein the ratio of naltrexone to oxycodone is from about 0.037:1 to about 0.296:1.

13. The oral dosage form of claim 1, wherein said opioid antagonist is naltrexone and said opioid agonist is codeine, wherein the ratio of naltrexone to codeine is from about 0.005:1 to about 0.044:1.

14. The oral dosage form of claim 1, wherein said opioid antagonist is naltrexone and said opioid agonist is hydromorphone, wherein the ratio of naltrexone to hydromorphone is from about 0.148:1 to about 1.185:1.

15. The oral dosage form of claim 1, wherein said opioid antagonist is naltrexone and said opioid agonist is levorphanol, wherein the ratio of naltrexone to levorphanol is from about 0.278:1 to about 2.222:1.

16. The oral dosage form of claim 1, wherein said opioid antagonist is naltrexone and said opioid agonist is meperidine, wherein the ratio of naltrexone to meperidine is from about 0.0037:1 to about 0.0296:1.

17. The oral dosage form of claim 1, wherein said opioid antagonist is naltrexone and said opioid agonist is methadone, wherein the ratio of naltrexone to methadone is from about 0.056:1 to about 0.444:1.

18. The oral dosage form of claim 1, wherein said opioid antagonist is naltrexone and said opioid agonist is morphine, wherein the ratio of naltrexone to morphine is from about 0.018:1 to about 0.148:1.

19. The oral dosage form of claim 1, wherein said opioid antagonist is naltrexone and said opioid agonist is oxycodone, wherein the ratio of naltrexone to oxycodone is from about 0.056:1 to about 0.222:1.

20. The oral dosage form of claim 1, wherein said opioid antagonist is naltrexone and said opioid agonist is codeine, wherein the ratio of naltrexone to codeine is from about 0.0083:1 to about 0.033:1.

21. A method of preventing oral abuse of an oral opioid formulation, comprising preparing an oral dosage form of claim 1 which comprises a therapeutically effective dose of an opioid agonist and incorporating therein an opioid antagonist in a ratio to said opioid agonist such that the oral dosage form is analgesically effective when administered orally, but (i) is aversive in physically dependent human subjects when administered at the same dose as said therapeutically effective dose; and (ii) maintains an analgesic but does not increase analgesic efficacy of the opioid agonist relative to the same therapeutic dose of opioid analgesic when administered to human patients without said opioid antagonist.

22. The method of claim 21, wherein said oral dosage form is aversive in physically dependent human subjects when administered at the same dose and at a higher dose than said therapeutically effective dose.

23. An oral dosage form, comprising an orally therapeutically effective dose of an opioid agonist, and an opioid antagonist, the dosage form having a ratio of opioid antagonist to opioid agonist that provides a combination product which is analgesically effective when the combination is administered orally, but which (i) is aversive in physically dependent human subjects when administered at the same dose and at a higher dose than said therapeutically effective dose; and (ii) maintains an analgesic effect but does not increase analgesic efficacy of the opioid agonist relative to the same therapeutic dose of opioid analgesic when administered to human patients without said opioid antagonist.

* * * * *